US007270977B2

(12) United States Patent
Aichinger et al.

(10) Patent No.: US 7,270,977 B2
(45) Date of Patent: Sep. 18, 2007

(54) POLYPEPTIDES FOR IDENTIFYING FUNGICIDALLY ACTIVE COMPOUNDS

(75) Inventors: Christian Aichinger, Köln (DE); Peter Schreier, Köln (DE); Volkhart Li, Velbert (DE); Arnd Voerste, Köln (DE); Karl-Heinz Kuck, Lagenfeld (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 10/313,371

(22) Filed: Dec. 6, 2002

(65) Prior Publication Data

US 2003/0228649 A1     Dec. 11, 2003

(30) Foreign Application Priority Data

Dec. 11, 2001   (DE)   ............................. 101 60 660

(51) Int. Cl.
*C12Q 1/18*   (2006.01)
(52) U.S. Cl. ...................... 435/32; 435/4; 435/7.31; 435/7.8; 435/26; 435/29
(58) Field of Classification Search ................ 435/4, 435/7.31, 7.8, 26, 29, 32
See application file for complete search history.

(56) References Cited

U.S. PATENT DOCUMENTS

| 5,976,848 A | 11/1999 | Davis et al. ................. 435/183 |
| 6,376,216 B1 | 4/2002 | Doval et al. ................ 435/69.1 |
| 6,391,603 B1 | 5/2002 | Pompejus et al. ........... 435/193 |

FOREIGN PATENT DOCUMENTS

| WO | 95/11969 | 5/1995 |
| WO | 97/44484 | 11/1997 |
| WO | 98/32847 | 7/1998 |
| WO | 98/37203 | 8/1998 |
| WO | 99/13094 | 3/1999 |
| WO | 99/33996 | 7/1999 |
| WO | 00/11189 | 3/2000 |

OTHER PUBLICATIONS

Cell, vol. 86, pp. 917-927, Sep. 20, 1996, Anion Exchanger 1 (Band 3) Is Required to Prevent Erythrocyte Membrane Surface Loss but Not to Form the Membrane Skeleton by L. L. Peters et al.
Biochemistry, month unavailable, 1999, 38, pp. 15388-15397, Species-Specific Inhibition of Inosine 5'-Monophosphate Dehydrogenase by Mycophenolic Acid by J. A. Digits and L. Hedstrom.
Current Medicinal Chemistry, month unavailable, 1999, 6, pp. 575-597, Mizoribine and Mycophenolate Mofetil by H. Ishikawa.
Current Medicinal Chemistry, month unavailable, 1999, 6, pp. 537-543, Differential Signatures of Bacterial and Mammaliam IMP Dehydrogenase Enzymes by R. Zhang et al.
Current Medicinal Chemistry; month unavailable, 1999, 6, pp. 519-536, IMP Dehydrogenase: Structural Aspects of Inhibitor Binding by B. M. Goldstein and T. D. Colby.

Antimicrobial Agents and Chemotherapy, vol. 41, No. 1, Jan. 1997, pp. 40-48, IMP Dehydrogenase from *Pneumoscystis carinii* as a Potential Drug Target by M. J. O'Gara et al.
Journal of Bacteriology, Apr. 1997, pp. 2331-2338, vol. 179, No. 7, Overexpression of a Cloned IMP Dehydrogenase Gene of *Candida albicans* Confers Resistance to the Specific Inhibitor Mycophenolic Acid by G. A. Köhler, T. C. White and N. Agabian.
The Journal of Anibiotics, vol. XXII, No. 4, pp. 165-169, Apr. 1969, Some Biological Properties of Mycophenolic Acid by T. Noto, M. Sawada, K. Ando and K. Koyama.
Farazi T et al: "Isolation and characterization of mycophenolic acid-resistant mutants of inosine-5'-monophosphate dehydrogenase." The Journal of Biological Chemistry. United States Jan. 10, 1997, Bd. 272, Nr. 2, Jan. 10, 1997, Seiten 961-965, XP002234558, ISSN: 0021-9258, das ganze Dokument.
Anderson W K et al: "Synthesis and modeling studies with monocyclic analogues of mycophenolic acid." Journal of Medicinal Chemistry. United States Jan. 5, 1996, Bd. 39, Nr. 1, Jan. 5, 1996, Seiten 46-55, XP002234559 ISSN: 0022-2623 das ganze Dokument.
Trilateral Project B3b Mutual understanding in search and examination-Report on Comparative study on biotechnology patent practices-Theme Comparative study on reach-through claims. Nov. 5-9, 2001, pp. 1-19 and 41-48.
Gene Bank Acc. No.: NP_ 013536 (Saccharomyces cerevisiae) submitted by the Department of Genetics, Stanford University, Saccharomyces Genome Database, Stanford, CA 94305-5120, Nov. 99.
Acta Chemica Sandinavic 1 3, (month unavailable) 19949, pp. 1343-1349, Erik rennerfelt, The Effect of Some Antibiotic Substances on the Germination of the Conidia of Polyporus annosus Fr.
Gen Bank Acc. No.: NP_009435 (Saccharomyces cerevisiae), submitted by National Center for Biotechnology, Information, NIH, Bethesda, MD 20894, USA, Nov. 99.
Gen Bank Acc. No.: NP_013656 (Saccharomyces cerevisiae), submitted by Department of Genetics, Stanford University, Saccharomyces Genome Database, Stanford, CA 94305-5120, Nov. 99.
Gen Bank Acc. No.: NP_012088 (Saccharomyces cerevisiae), submitted by the Department of Genetics, Stanford University, Saccaromyces Genome Database, Stanford, CA 29305-5120, Nov. 99.
Gen Bank Acc. No.: XP_711825 (Candida albicans) submitted by Kohler et al, Uni Würzburg 1997.

(Continued)

*Primary Examiner*—Jennifer E. Graser
(74) *Attorney, Agent, or Firm*—Raymond J. Harmuth

(57) ABSTRACT

The invention relates to polypeptides from phytopathogenic fungi with the biological activity of an inosine monophosphate dehydrogenase, to nucleic acids encoding them, to the use of the polypeptides and nucleic acids for identifying modulators of the polypeptides, to methods for identifying such modulators, and to the use of these modulators as fungicides.

4 Claims, 7 Drawing Sheets

OTHER PUBLICATIONS

Figure 1:
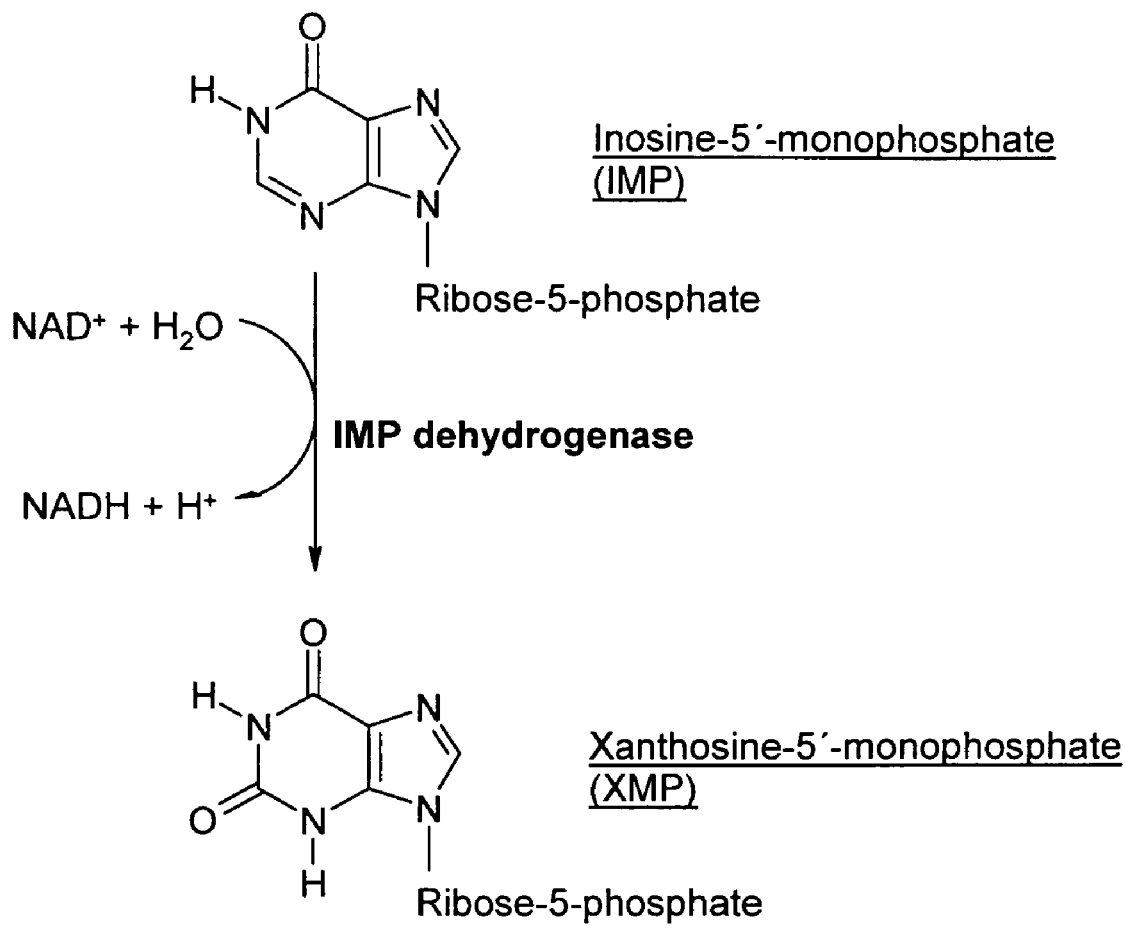

Gen Bank Acc. No.: AF196975 (Pneumocystis carinii), submitted by Pharmacology, Indiana University School of Medicine, 635 Barnhill Dr., Indianapolis, IN 46202, USA, Oct. 1999.

Sequenzvergleich auf Aminosäureebene der Sequenz von Ustilago maydis (Streitpatent, SEQ ID No.:2 mit D3, D9, D10, D11, D12 und D13.

Infection and Immunity, Nov. 1999, vol. 67, No. 11, pp. 3157-6160, Charles F. Thomas, Jr. et al, "Analysis of Pneumocystis *carinii* introns".

Biochemical Society Transactions, (month unavailable) 1986, p. 260, Joseph A. Gallagher et al, "The action of mycophenotic acid on *Candida albicans*".

Congrés International De Botanique, (month unavailable) 1954, pp. 111-113, P. W. Brian, "Some Antifungal natibiotics".

```
              10         20         30         40         50
U.m.Impl     MPASNGIQLP QDEAVLSPSQ ALEHLKTYTY GDGLSMAELI DSRQHGGLTY
S.c.IMH3     ---------- MSAAPLDYKK ALEHLKTYSS KDGLSVQELM DSTTRGGLTY
S.c.IMH2     ---------- -MAAVRDYKT ALEFAKSLPR LDGLSVQELM DSKTRGGLTY
S.c.IMH1     ---------- -MAAIRDYKT ALDFTKSLPR PDGLSVQELM DSKIRGGLTY
H.s.IMD1     ---------- ----MADY-- LISGGTGYVP EDGLTAQQLF AS--ADDLTY
A.t.IMD      ---------- ---------- ------MSGF EDGFSAEKLF SQG--YSYTY
              60         70         80         90         100
U.m.Impl     NDFLVLPGFI NFAASDVSLR TKVTKNVTLN TPFLSSPMDT VTETEMAIAM
S.c.IMH3     NDFLVLPGLV NFPSSAVSLQ TKLTKKITLN TPFVSSPMDT VTEADMAIYM
S.c.IMH2     NDFLVLPGLV DFPSSEVSLQ TKLTRNITLN TPFVSSPMDT VTESEMAIFM
S.c.IMH1     NDFLILPGLV DFASSEVSLQ TKLTRNITLN IPLVSSPMDT VTESEMATFM
H.s.IMD1     NDFLILPGFI DFIADEVDLT SALTRKITLK TPLISSPMDT VTEADMAIAM
A.t.IMD      DDVIFLPHFI DFSTDAVSLS TRLSKRVPLS IPCVASPMDT VSESHMAAAM
              110        120        130        140        150
U.m.Impl     GLMGGMGVIH NNMSPQEQAS VVRKVKKYEN GFITEPLCLD PKATVGDVLD
S.c.IMH3     ALLGGIGFIH HNCTPKEQAS MVKKVKMFEN GFINSPIVIS PTTTVGEVKV
S.c.IMH2     ALLGGIGFIH HNCTPEDQAD MVRRVKNYEN GFINNPIVIS PTTTVGEAKS
S.c.IMH1     ALLGGIGFIH HNCTPEDQAD MVRRVKNYEN GFINNPIVIS PTTTVGEAKS
H.s.IMD1     ALMGGIGFIH HNCTPEFQAN EVRKVKNFEQ GFITDPVVLS PSHTVGDVLE
A.t.IMD      AALGGIGIVH YNCDIDTQAS VIRHAKSLQV PIASDAVFKC PEHQIGSVDD
              160        170        180        190        200
U.m.Impl     VKERLGFGGI PITDTGAMHG KLLGIVTARD VQFR---DTT LPLSEVMTT-
S.c.IMH3     MKRKFGFSGF PVTEDGKCPG KLVGLVTSRD IQFLE--DDS LVVSEVMTK-
S.c.IMH2     MKERFGFSGF PVTEDGKRNG KLMGIVTSRD IQFVE--DNS LLVQDVMTK-
S.c.IMH1     MKEKYGFAGF PVTTDGKRNA KLVGVITSRD IQFVE--DNS LLVQDVMTK-
H.s.IMD1     AKMRHGFSGI PITETGTMGS KLVGIVTSRD IDFLAEKDHT TLLSEVMTPR
A.t.IMD      FGP---SSFV FVSQTGTLTP KLLGYVSKSE WSSMKDDQKE VKIYDYMKSC
              210        220        230        240        250
U.m.Impl     --DLVTAKQG VTLEQANTIL RDSKKGKLPI VDAEGRLVAL LARSDLLKNQ
S.c.IMH3     --NPVTGIKG ITLKEGNEIL KQTKKGKLLI VDDNGNLVSM LSRADLMKNQ
S.c.IMH2     --NPVTGAQG ITLSEGNEIL KKIKKGKLLI VDDNGNLVSM LSRTDLMKNQ
S.c.IMH1     --NPVTGAQG ITLSEGNEIL KKIKKGRLLV VDEKGNLVSM LSRTDLMKNQ
H.s.IMD1     -IELVVAPAG VTLKEANEIL QRSKKGKLPI VNDCDELVAI IARTDLKKNR
A.t.IMD      ENKDYYVPWD IDLDKIEAVL EDKQKG-FVV LEKEGETVNV VTKDDVERVK
              260        270        280        290        300
U.m.Impl     NFP-LASKRP ES-KQLYCAA AIGTRPSDRE RLSLLVEAGL DVVILDSSQG
S.c.IMH3     NYP-LASKSA TT-KQLLCGA AIGTIEADKE RLRLLVEAGL DVVILDSSQG
S.c.IMH2     NYP-LASKSA TT-KQLLCGA AIGTIDADKE RLRLLVEAGL DVVILDSSQG
```

```
S.c.IMH1    NYP-LASKSA  NT-KQLLCGA  SIGTMDADKE  RLRLLVKAGL  DVVILDSSQG
H.s.IMD1    DYP-LASKDS  Q--KQLLCGA  AVGTREDDKY  RLDLLTQAGV  DVIVLDSSQG
A.t.IMD     GYPKLGSGTV  GADKKWMVGA  AIGTRESDKE  RLEHLVKAGA  NVVVLDSSQG
                   310         320         330         340         350
U.m.Imp1    NSVYQIEMIQ  WIKQTYPQID  VVAGNVVTRE  QAASLIAAGA  DALRVGMGSG
S.c.IMH3    NSVFQLNMIK  WIKETFPDLE  IIAGNVATRE  QAANLIAAGA  DGLRIGMGSG
S.c.IMH2    NSIFQLNMIK  WIKETFPDLE  IIAGNVATRE  QAANLIAAGA  DGLRIGMGSG
S.c.IMH1    NSIFELNMLK  WVKESFPGLE  VIAGNVVTRE  QAANLIAAGA  DGLRIGMGTG
H.s.IMD1    NSVYQIAMVH  YIKQKYPHLQ  VIGGNVVTAA  QAKNLIDAGV  DGLRVGMGCG
A.t.IMD     NSIYQLEMIK  YVKNTYPELD  VVGGNVVTMY  QAENLIKAGV  DGLRVGMGSG
                   360         370         380         390         400
U.m.Imp1    SICITQEVMA  VGRPQGTAVH  AVAEFASKFG  VPVIADGGIS  NVGHIAKALA
S.c.IMH3    SICITQEVMA  CGRPQGTAVY  NVCQFANQFG  VPCMADGGVQ  NIGHITKALA
S.c.IMH2    SICITQEVMA  CGRPQGTAVY  NVCEFANQFG  IPCMADGGVQ  NIGHITKALA
S.c.IMH1    SICITQEVMA  CGRPQGTAVY  NVCEFANQFG  VPCMADGGVQ  NIGHITKALA
H.s.IMD1    SICITQEVMA  CGRPQGTAVY  KVAEYARRFG  VPIIADGGIQ  TVGHVVKALA
A.t.IMD     SICTTQEVCA  VGRGQATAVY  KVSTLAAQHG  VPVIADGGIS  NSGHIVKALV
                   410         420         430         440         450
U.m.Imp1    LGASAVMMGG  LLAGTNESPG  DYFYRDGKRL  KGYRGMGSIE  AMEHQKKGKI
S.c.IMH3    LGSSTVMMGG  MLAGTTESPG  EYFYKDGKRL  KAYRGMGSID  AM--QKTG--
S.c.IMH2    LGSSTVMMGG  MLAGTTESPG  EYFYQDGKRL  KAYRGMGSID  AM--QKTG--
S.c.IMH1    LGSSTVMMGG  MLAGTTESPG  EYFYQDGKRL  KAYRGMGSID  AM--QKTG--
H.s.IMD1    LGASTVMMGS  LLAATTEAPG  EYFFSDGVRL  KKYRGMGSLD  AM--EKSS--
A.t.IMD     LGASTVMMGS  FLAGSTEAPG  AYEYRNGRRV  KKYRGMGSLE  AM---TKG--
                   460         470         480         490         500
U.m.Imp1    AGATGKGAAK  ADKVATDENA  ATQRYFSESD  AVKVAQGVAG  AVQDKGSVKK
S.c.IMH3    ----NKG---  --------NA  STSRYFSESD  SVLVAQGVSG  AVVDKGSIKK
S.c.IMH2    ----TKG---  --------NA  STSRYFSESD  SVLVAQGVSG  AVVDKGSIKK
S.c.IMH1    ----TKG---  --------NA  STSRYFSESD  SVLVAQGVSG  AVVDKGSIKK
H.s.IMD1    ----------  ---------S  SQKRYFSEGD  KVKIAQGVSG  SIQDKGSIQK
A.t.IMD     ----------  ----------  SDQRYLGDTA  KLKIAQGVVG  AVADKGSVLK
                   510         520         530         540         550
U.m.Imp1    FLPYLYTGLQ  HSLQDMGVPH  LYQLRSAVAS  GQVRFELRTA  SAQVEGGVHG
S.c.IMH3    FIPYLYNGLQ  HSCQDIGCES  LTSLKENVQN  GEVRFEFRTA  SAQLEGGVHN
S.c.IMH2    FIPYLYNGLQ  HSCQDIGYKS  LTLLKENVQS  GKVRFEFRTA  SAQLEGGVHN
S.c.IMH1    FIPYLYNGLQ  HSCQDIGCRS  LTLLKNNVQR  GKVRFEFRTA  SAQLEGGVHN
H.s.IMD1    FVPYLIAGIQ  HGCQDIGARS  LSVLRSMMYS  GELKFEKRTM  SAQIEGGVHG
A.t.IMD     FIPYTMHAVK  QGFQDLGASS  LQSAHELLRD  NTLRLEARTG  AAQIEGGIHG
560 562
```

```
U.m.Imp1    LHSYEKRLFS  SL
S.c.IMH3    LHSYEKRLYN  --
S.c.IMH2    LHSYEKRLHN  --
S.c.IMH1    LHSYEKRLHN  --
H.s.IMD1    LHSYEKRLY-  --
A.t.IMD     LVSYEKKSF-  --
```

Figure 5

SEQUENCE LISTING

<160> NUMBER OF SEQ ID NOS: 6

<210> SEQ ID NO 1
<211> LENGTH: 3063
<212> TYPE: DNA
<213> ORGANISM: Ustilago maydis
<220> FEATURE:
<221> NAME/KEY: CDS
<222> LOCATION: (582)..(1071)
<223> OTHER INFORMATION:
<220> FEATURE:
<221> NAME/KEY: CDS
<222> LOCATION: (1412)..(2580)
<223> OTHER INFORMATION:

<400> SEQUENCE: 1

```
ttcacgattt acgatttacg attcgcgatt cacgattcat gattcacgat tcacgacgtt         60
ttacgatgtg atttgtggtg caagcgcgca ctctctcgac gattgaacgg agcaaactcg        120
tcgggcgtaa ctcgtgactg tagctcgtgg ctagacgctt gccaggtgag acgggctcgg        180
tttgcttgac gtgttcacat cgcgtgggtt gcggcgctag gtcaatcacg aatccttttt        240
cattcaatca ctgaatgata atataatttt gcccacctta gagaaagaag aaacgaaagc        300
cttaatcccg atctggcagc tagatttttt gatttttttt tttcgcttac acaaactgtg        360
agagggagag agttgaaact ttttttttcc ctacatggtg gctaaaagtg gctagggtt         420 actctccctc tcgtggtcgt tagcagcgaa gagaagcgaa gcgaagtaca aaggcatcca        480
atgccagagc gacatcttcc ttcttaaact gttcttcgcc aaaagagcca cccacttcca        540 acatacctt cctcgccctt cacctcccat catccatcaa a atg cct gct agc aac        596
                                              Met Pro Ala Ser Asn
                                                1               5 ggt att cag ctc cct cag gac gaa gcg gtc ctt tcg cct tct cag gcg        644
Gly Ile Gln Leu Pro Gln Asp Glu Ala Val Leu Ser Pro Ser Gln Ala
                 10                  15                  20 ctt gag cac ctc aag acc tac act tac ggc gat ggt ctc agc atg gcc        692
Leu Glu His Leu Lys Thr Tyr Thr Tyr Gly Asp Gly Leu Ser Met Ala
             25                  30                  35 gag ctc atc gac tcg cgt cag cac ggt ggt ctc acc tac aat gac ttt        740
Glu Leu Ile Asp Ser Arg Gln His Gly Gly Leu Thr Tyr Asn Asp Phe
         40                  45                  50 ctc gtt ctg ccc ggt ttc atc aac ttt gct gct tcg gac gtc agc ctg        788
Leu Val Leu Pro Gly Phe Ile Asn Phe Ala Ala Ser Asp Val Ser Leu
     55                  60                  65 cgc acc aag gtg acc aag aac gtt acg ctc aac acg cct ttc ctc tcg        836
Arg Thr Lys Val Thr Lys Asn Val Thr Leu Asn Thr Pro Phe Leu Ser
 70                  75                  80                  85 tcg ccc atg gac acg gtt acc gag acc gag atg gcg atc gca atg ggc        884
Ser Pro Met Asp Thr Val Thr Glu Thr Glu Met Ala Ile Ala Met Gly
                 90                  95                 100 ttg atg ggc ggt atg ggt gtc att cac aac aac atg agc cct cag gag        932
Leu Met Gly Gly Met Gly Val Ile His Asn Asn Met Ser Pro Gln Glu
            105                 110                 115 cag gct agc gtt gtg cgc aag gtc aag aag tac gag aac ggt ttc atc        980
Gln Ala Ser Val Val Arg Lys Val Lys Lys Tyr Glu Asn Gly Phe Ile
        120                 125                 130 acc gaa cct ctc tgc ctc gac ccc aag gcc acc gtc ggt gac gtt ctc       1028
Thr Glu Pro Leu Cys Leu Asp Pro Lys Ala Thr Val Gly Asp Val Leu
    135                 140                 145 gat gtc aag gag cgt ctg ggt ttt ggt ggt att cct atc act g              1071
Asp Val Lys Glu Arg Leu Gly Phe Gly Gly Ile Pro Ile Thr
```

```
Asp Val Lys Glu Arg Leu Gly Phe Gly Gly Ile Pro Ile Thr
150                 155                 160 gtaagttgtc gatcgaatta aaacagcttt ctacttcttc tttctcctcc tcctccccttt      1131 ccccggacta cccgtcccgc tgcaccgctc gacaatcttg gtcgacctcg cctcttcact      1191
gctacgctct cactcaccaa aggatgaaac aaccgtattg catataacct tcgttcttcc      1251
gagcctctcc cttagacttg ggagagtgtg tgcggatgcg attttttcaac tctgatttgc     1311 ctctcattcg atcgctgttc ggtctcgaca tggttctctc gatcttttat gctgacctcg      1371
atcttctctg tgtttcgcat accccatcga tccgacgtag ac  act ggt gcg atg       1425
                                              Asp Thr Gly Ala Met
                                                           165 cac ggc aag ctt ctc ggt atc gtc act gct cgt gac gtc cag ttc cgt       1473
His Gly Lys Leu Leu Gly Ile Val Thr Ala Arg Asp Val Gln Phe Arg
         170                 175                 180 gat acc acg ctt ccg ctt tcc gag gtc atg acc acc gac ctt gtc acc       1521
Asp Thr Thr Leu Pro Leu Ser Glu Val Met Thr Thr Asp Leu Val Thr
185                 190                 195                 200 gcc aag cag gga gtc acg ctc gag cag gcc aac act atc ctg cgt gac       1569
Ala Lys Gln Gly Val Thr Leu Glu Gln Ala Asn Thr Ile Leu Arg Asp
                205                 210                 215 agc aaa aag ggc aag ctc ccc atc gtc gac gcc gag ggc cgc ctt gtt       1617
Ser Lys Lys Gly Lys Leu Pro Ile Val Asp Ala Glu Gly Arg Leu Val
        220                 225                 230 gcc ctg ctc gct cgc tct gac ttg ctc aag aat caa aac ttc cct ctc       1665
Ala Leu Leu Ala Arg Ser Asp Leu Leu Lys Asn Gln Asn Phe Pro Leu
        235                 240                 245 gcc tcc aag cgt ccc gaa agc aag cag ctt tac tgt gcc gct gcc atc       1713
Ala Ser Lys Arg Pro Glu Ser Lys Gln Leu Tyr Cys Ala Ala Ala Ile
250                 255                 260 ggc act cgt ccc tca gac cgt gaa cgt ctc agt ctt ctt gta gag gct       1761
Gly Thr Arg Pro Ser Asp Arg Glu Arg Leu Ser Leu Leu Val Glu Ala
265                 270                 275                 280 gga ttg gac gtt gtc atc ctc gac tcg tcc cag ggt aac tcg gtg tat       1809
Gly Leu Asp Val Val Ile Leu Asp Ser Ser Gln Gly Asn Ser Val Tyr
                285                 290                 295 cag atc gaa atg atc cag tgg atc aag cag acc tac ccg cag atc gac       1857
Gln Ile Glu Met Ile Gln Trp Ile Lys Gln Thr Tyr Pro Gln Ile Asp
        300                 305                 310 gtt gtc gcc ggt aac gtc gtc aca cga gag cag gct gcc agc ctg atc       1905
Val Val Ala Gly Asn Val Val Thr Arg Glu Gln Ala Ala Ser Leu Ile
        315                 320                 325 gcc gct ggt gct gac gcc ctt cgt gtc ggc atg ggt tcc ggt tcg atc       1953
Ala Ala Gly Ala Asp Ala Leu Arg Val Gly Met Gly Ser Gly Ser Ile
330                 335                 340 tgc atc acc cag gaa gtg atg gct gtc ggt cga cct cag ggt acc gcc       2001
Cys Ile Thr Gln Glu Val Met Ala Val Gly Arg Pro Gln Gly Thr Ala
345                 350                 355                 360 gtc cac gcc gtt gct gag ttc gcc tcc aag ttt ggc gtc ccc gtc atc       2049
Val His Ala Val Ala Glu Phe Ala Ser Lys Phe Gly Val Pro Val Ile
                365                 370                 375 gcc gat ggt gga att tcc aat gtc ggt cac atc gcc aaa gct ctc gca       2097
Ala Asp Gly Gly Ile Ser Asn Val Gly His Ile Ala Lys Ala Leu Ala
        380                 385                 390 ctc ggt gct tcc gcc gtc atg atg gga ggc ttg ctc gcc gga acc aac       2145
Leu Gly Ala Ser Ala Val Met Met Gly Gly Leu Leu Ala Gly Thr Asn
        395                 400                 405 gaa tcc ccc ggt gac tac ttc tat cgc gac ggt aag cgt ctc aag ggt       2193
Glu Ser Pro Gly Asp Tyr Phe Tyr Arg Asp Gly Lys Arg Leu Lys Gly
```

-continued

```
       410                 415                 420
tac cgt ggt atg gga tcc atc gaa gcc atg gag cac cag aag aag ggc     2241
Tyr Arg Gly Met Gly Ser Ile Glu Ala Met Glu His Gln Lys Lys Gly
425                 430                 435                 440 aag atc gcc ggc gcc acc ggt aaa ggt gct gcc aag gct gac aag gtt     2289
Lys Ile Ala Gly Ala Thr Gly Lys Gly Ala Ala Lys Ala Asp Lys Val
                445                 450                 455 gct acc gac gaa aac gcc gct acg cag cga tac ttt tct gaa agc gac     2337
Ala Thr Asp Glu Asn Ala Ala Thr Gln Arg Tyr Phe Ser Glu Ser Asp
            460                 465                 470 gcc gtc aag gtc gcc cag ggc gtt gca ggt gct gtg cag gac aag ggc     2385
Ala Val Lys Val Ala Gln Gly Val Ala Gly Ala Val Gln Asp Lys Gly
        475                 480                 485 tcg gtc aag aag ttc ttg cct tac ctg tac acc ggt ctg caa cac tcg     2433
Ser Val Lys Lys Phe Leu Pro Tyr Leu Tyr Thr Gly Leu Gln His Ser
    490                 495                 500 ttg cag gac atg ggt gtc cca cac ctc tac cag ttg cgc tct gca gtg     2481
Leu Gln Asp Met Gly Val Pro His Leu Tyr Gln Leu Arg Ser Ala Val
505                 510                 515                 520 gcc tcg ggc cag gtg agg ttc gag ttg agg acc gca agc gcc cag gtc     2529
Ala Ser Gly Gln Val Arg Phe Glu Leu Arg Thr Ala Ser Ala Gln Val
                525                 530                 535 gag ggt ggt gtc cac ggg ctt cac agc tac gag aag cgt ctg ttc tct     2577
Glu Gly Gly Val His Gly Leu His Ser Tyr Glu Lys Arg Leu Phe Ser
            540                 545                 550 tcg tagggttcga gttgaggacc gcaagcgccc aggtcgaggg tggtgtccac          2630
Ser gggcttcaca gctacgagaa gcgtctgttc tcttcgtaga tgtttccctt ttaagaagca   2690
cccatctttg gcaagacaaa caatctcatt ttgtctcttg ccaaatcgaa accatgaggc   2750
tcgaccggac ccatcgtgtc aacaaagatc tcagctttgt ggccttgtct acacgtgcca   2810
gcagctcgcc tctctatctc tatcatttgt actttagtcg cttttgtttc acccttcatt   2870
ctgctcaaaa gatgtgttat gaatcgtgat tctagcctag cgctcttttc agcgctgctt   2930
ggcaaagtct gtggatgcag ttgaagtgag tcacagagta aaagcgagtg gatctttggt   2990
gcctgtttgg atgagttgaa gtaagatcga gaaatgttag ggtacgcgaa ctttcgagaa   3050
agacttcggg gaa                                                      3063
```

<210> SEQ ID NO 2
<211> LENGTH: 553
<212> TYPE: PRT
<213> ORGANISM: Ustilago maydis

<400> SEQUENCE: 2

```
Met Pro Ala Ser Asn Gly Ile Gln Leu Pro Gln Asp Glu Ala Val Leu
1               5                   10                  15

Ser Pro Ser Gln Ala Leu Glu His Leu Lys Thr Tyr Thr Tyr Gly Asp
                20                  25                  30

Gly Leu Ser Met Ala Glu Leu Ile Asp Ser Arg Gln His Gly Gly Leu
            35                  40                  45

Thr Tyr Asn Asp Phe Leu Val Leu Pro Gly Phe Ile Asn Phe Ala Ala
        50                  55                  60

Ser Asp Val Ser Leu Arg Thr Lys Val Thr Lys Asn Val Thr Leu Asn
65                  70                  75                  80

Thr Pro Phe Leu Ser Ser Pro Met Asp Thr Val Thr Glu Thr Glu Met
                85                  90                  95
```

-continued

```
Ala Ile Ala Met Gly Leu Met Gly Gly Met Gly Val Ile His Asn Asn
            100                 105                 110

Met Ser Pro Gln Glu Gln Ala Ser Val Val Arg Lys Val Lys Lys Tyr
        115                 120                 125

Glu Asn Gly Phe Ile Thr Glu Pro Leu Cys Leu Asp Pro Lys Ala Thr
        130                 135                 140

Val Gly Asp Val Leu Asp Val Lys Glu Arg Leu Gly Phe Gly Gly Ile
145                 150                 155                 160

Pro Ile Thr Asp Thr Gly Ala Met His Gly Lys Leu Leu Gly Ile Val
                165                 170                 175

Thr Ala Arg Asp Val Gln Phe Arg Asp Thr Thr Leu Pro Leu Ser Glu
            180                 185                 190

Val Met Thr Thr Asp Leu Val Thr Ala Lys Gln Gly Val Thr Leu Glu
        195                 200                 205

Gln Ala Asn Thr Ile Leu Arg Asp Ser Lys Lys Gly Lys Leu Pro Ile
        210                 215                 220

Val Asp Ala Glu Gly Arg Leu Val Ala Leu Leu Ala Arg Ser Asp Leu
225                 230                 235                 240

Leu Lys Asn Gln Asn Phe Pro Leu Ala Ser Lys Arg Pro Glu Ser Lys
                245                 250                 255

Gln Leu Tyr Cys Ala Ala Ala Ile Gly Thr Arg Pro Ser Asp Arg Glu
            260                 265                 270

Arg Leu Ser Leu Leu Val Glu Ala Gly Leu Asp Val Val Ile Leu Asp
        275                 280                 285

Ser Ser Gln Gly Asn Ser Val Tyr Gln Ile Glu Met Ile Gln Trp Ile
        290                 295                 300

Lys Gln Thr Tyr Pro Gln Ile Asp Val Val Ala Gly Asn Val Val Thr
305                 310                 315                 320

Arg Glu Gln Ala Ala Ser Leu Ile Ala Ala Gly Ala Asp Ala Leu Arg
                325                 330                 335

Val Gly Met Gly Ser Gly Ser Ile Cys Ile Thr Gln Glu Val Met Ala
            340                 345                 350

Val Gly Arg Pro Gln Gly Thr Ala Val His Ala Val Ala Glu Phe Ala
        355                 360                 365

Ser Lys Phe Gly Val Pro Val Ile Ala Asp Gly Gly Ile Ser Asn Val
        370                 375                 380

Gly His Ile Ala Lys Ala Leu Ala Leu Gly Ala Ser Ala Val Met Met
385                 390                 395                 400

Gly Gly Leu Leu Ala Gly Thr Asn Glu Ser Pro Gly Asp Tyr Phe Tyr
                405                 410                 415

Arg Asp Gly Lys Arg Leu Lys Gly Tyr Arg Gly Met Gly Ser Ile Glu
            420                 425                 430

Ala Met Glu His Gln Lys Lys Gly Lys Ile Ala Gly Ala Thr Gly Lys
        435                 440                 445

Gly Ala Ala Lys Ala Asp Lys Val Ala Thr Asp Glu Asn Ala Ala Thr
        450                 455                 460

Gln Arg Tyr Phe Ser Glu Ser Asp Ala Val Lys Val Ala Gln Gly Val
465                 470                 475                 480

Ala Gly Ala Val Gln Asp Lys Gly Ser Val Lys Lys Phe Leu Pro Tyr
                485                 490                 495

Leu Tyr Thr Gly Leu Gln His Ser Leu Gln Asp Met Gly Val Pro His
            500                 505                 510

Leu Tyr Gln Leu Arg Ser Ala Val Ala Ser Gly Gln Val Arg Phe Glu
```

```
                  515                 520                     525
Leu Arg Thr Ala Ser Ala Gln Val Glu Gly Gly Val His Gly Leu His
    530                 535                 540

Ser Tyr Glu Lys Arg Leu Phe Ser Ser
545                 550

<210> SEQ ID NO 3
<211> LENGTH: 1662
<212> TYPE: DNA
<213> ORGANISM: Ustilago maydis
<220> FEATURE:
<221> NAME/KEY: CDS
<222> LOCATION: (1)..(1659)

<400> SEQUENCE: 3 atg cct gct agc aac ggt att cag ctc cct cag gac gaa gcg gtc ctt    48
Met Pro Ala Ser Asn Gly Ile Gln Leu Pro Gln Asp Glu Ala Val Leu
1               5                   10                  15 tcg cct tct cag gcg ctt gag cac ctc aag acc tac act tac ggc gat    96
Ser Pro Ser Gln Ala Leu Glu His Leu Lys Thr Tyr Thr Tyr Gly Asp
                20                  25                  30 ggt ctc agc atg gcc gag ctc atc gac tcg cgt cag cac ggt ggt ctc    144
Gly Leu Ser Met Ala Glu Leu Ile Asp Ser Arg Gln His Gly Gly Leu
            35                  40                  45 acc tac aat gac ttt ctc gtt ctg ccc ggt ttc atc aac ttt gct gct    192
Thr Tyr Asn Asp Phe Leu Val Leu Pro Gly Phe Ile Asn Phe Ala Ala
        50                  55                  60 tcg gac gtc agc ctg cgc acc aag gtg acc aag aac gtt acg ctc aac    240
Ser Asp Val Ser Leu Arg Thr Lys Val Thr Lys Asn Val Thr Leu Asn
65                  70                  75                  80 acg cct ttc ctc tcg tcg ccc atg gac acg gtt acc gag acc gag atg    288
Thr Pro Phe Leu Ser Ser Pro Met Asp Thr Val Thr Glu Thr Glu Met
                85                  90                  95 gcg atc gca atg ggc ttg atg ggc ggt atg ggt gtc att cac aac aac    336
Ala Ile Ala Met Gly Leu Met Gly Gly Met Gly Val Ile His Asn Asn
                100                 105                 110 atg agc cct cag gag cag gct agc gtt gtg cgc aag gtc aag aag tac    384
Met Ser Pro Gln Glu Gln Ala Ser Val Val Arg Lys Val Lys Lys Tyr
            115                 120                 125 gag aac ggt ttc atc acc gaa cct ctc tgc ctc gac ccc aag gcc acc    432
Glu Asn Gly Phe Ile Thr Glu Pro Leu Cys Leu Asp Pro Lys Ala Thr
        130                 135                 140 gtc ggt gac gtt ctc gat gtc aag gag cgt ctg ggt ttt ggt ggt att    480
Val Gly Asp Val Leu Asp Val Lys Glu Arg Leu Gly Phe Gly Gly Ile
145                 150                 155                 160 cct atc act gac act ggt gcg atg cac ggc aag ctt ctc ggt atc gtc    528
Pro Ile Thr Asp Thr Gly Ala Met His Gly Lys Leu Leu Gly Ile Val
                165                 170                 175 act gct cgt gac gtc cag ttc cgt gat acc acg ctt ccg ctt tcc gag    576
Thr Ala Arg Asp Val Gln Phe Arg Asp Thr Thr Leu Pro Leu Ser Glu
            180                 185                 190 gtc atg acc acc gac ctt gtc acc gcc aag cag gga gtc acg ctc gag    624
Val Met Thr Thr Asp Leu Val Thr Ala Lys Gln Gly Val Thr Leu Glu
        195                 200                 205 cag gcc aac act atc ctg cgt gac agc aaa aag ggc aag ctc ccc atc    672
Gln Ala Asn Thr Ile Leu Arg Asp Ser Lys Lys Gly Lys Leu Pro Ile
    210                 215                 220 gtc gac gcc gag ggc cgc ctt gtt gcc ctg ctc gct cgc tct gac ttg    720
Val Asp Ala Glu Gly Arg Leu Val Ala Leu Leu Ala Arg Ser Asp Leu
225                 230                 235                 240
```

```
ctc aag aat caa aac ttc cct ctc gcc tcc aag cgt ccc gaa agc aag         768
Leu Lys Asn Gln Asn Phe Pro Leu Ala Ser Lys Arg Pro Glu Ser Lys
                245                 250                 255 cag ctt tac tgt gcc gct gcc atc ggc act cgt ccc tca gac cgt gaa         816
Gln Leu Tyr Cys Ala Ala Ala Ile Gly Thr Arg Pro Ser Asp Arg Glu
            260                 265                 270 cgt ctc agt ctt ctt gta gag gct gga ttg gac gtt gtc atc ctc gac         864
Arg Leu Ser Leu Leu Val Glu Ala Gly Leu Asp Val Val Ile Leu Asp
        275                 280                 285 tcg tcc cag ggt aac tcg gtg tat cag atc gaa atg atc cag tgg atc         912
Ser Ser Gln Gly Asn Ser Val Tyr Gln Ile Glu Met Ile Gln Trp Ile
    290                 295                 300 aag cag acc tac ccg cag atc gac gtt gtc gcc ggt aac gtc gtc aca         960
Lys Gln Thr Tyr Pro Gln Ile Asp Val Val Ala Gly Asn Val Val Thr
305                 310                 315                 320 cga gag cag gct gcc agc ctg atc gcc gct ggt gct gac gcc ctt cgt        1008
Arg Glu Gln Ala Ala Ser Leu Ile Ala Ala Gly Ala Asp Ala Leu Arg
                325                 330                 335 gtc ggc atg ggt tcc ggt tcg atc tgc atc acc cag gaa gtg atg gct        1056
Val Gly Met Gly Ser Gly Ser Ile Cys Ile Thr Gln Glu Val Met Ala
            340                 345                 350 gtc ggt cga cct cag ggt acc gcc gtc cac gcc gtt gct gag ttc gcc        1104
Val Gly Arg Pro Gln Gly Thr Ala Val His Ala Val Ala Glu Phe Ala
        355                 360                 365 tcc aag ttt ggc gtc ccc gtc atc gcc gat ggt gga att tcc aat gtc        1152
Ser Lys Phe Gly Val Pro Val Ile Ala Asp Gly Gly Ile Ser Asn Val
    370                 375                 380 ggt cac atc gcc aaa gct ctc gca ctc ggt gct tcc gcc gtc atg atg        1200
Gly His Ile Ala Lys Ala Leu Ala Leu Gly Ala Ser Ala Val Met Met
385                 390                 395                 400 gga ggc ttg ctc gcc gga acc aac gaa tcc ccc ggt gac tac ttc tat        1248
Gly Gly Leu Leu Ala Gly Thr Asn Glu Ser Pro Gly Asp Tyr Phe Tyr
                405                 410                 415 cgc gac ggt aag cgt ctc aag ggt tac cgt ggt atg gga tcc atc gaa        1296
Arg Asp Gly Lys Arg Leu Lys Gly Tyr Arg Gly Met Gly Ser Ile Glu
            420                 425                 430 gcc atg gag cac cag aag aag ggc aag atc gcc ggc gcc acc ggt aaa        1344
Ala Met Glu His Gln Lys Lys Gly Lys Ile Ala Gly Ala Thr Gly Lys
        435                 440                 445 ggt gct gcc aag gct gac aag gtt gct acc gac gaa aac gcc gct acg        1392
Gly Ala Ala Lys Ala Asp Lys Val Ala Thr Asp Glu Asn Ala Ala Thr
    450                 455                 460 cag cga tac ttt tct gaa agc gac gcc gtc aag gtc gcc cag ggc gtt        1440
Gln Arg Tyr Phe Ser Glu Ser Asp Ala Val Lys Val Ala Gln Gly Val
465                 470                 475                 480 gca ggt gct gtg cag gac aag ggc tcg gtc aag aag ttc ttg cct tac        1488
Ala Gly Ala Val Gln Asp Lys Gly Ser Val Lys Lys Phe Leu Pro Tyr
                485                 490                 495 ctg tac acc ggt ctg caa cac tcg ttg cag gac atg ggt gtc cca cac        1536
Leu Tyr Thr Gly Leu Gln His Ser Leu Gln Asp Met Gly Val Pro His
            500                 505                 510 ctc tac cag ttg cgc tct gca gtg gcc tcg ggc cag gtg agg ttc gag        1584
Leu Tyr Gln Leu Arg Ser Ala Val Ala Ser Gly Gln Val Arg Phe Glu
        515                 520                 525 ttg agg acc gca agc gcc cag gtc gag ggt ggt gtc cac ggg ctt cac        1632
Leu Arg Thr Ala Ser Ala Gln Val Glu Gly Gly Val His Gly Leu His
    530                 535                 540 agc tac gag aag cgt ctg ttc tct tcg tag                                1662
Ser Tyr Glu Lys Arg Leu Phe Ser Ser
545                 550
```

<210> SEQ ID NO 4

<211> LENGTH: 553
<212> TYPE: PRT
<213> ORGANISM: Ustilago maydis

<400> SEQUENCE: 4

```
Met Pro Ala Ser Asn Gly Ile Gln Leu Pro Gln Asp Glu Ala Val Leu
1               5                   10                  15

Ser Pro Ser Gln Ala Leu Glu His Leu Lys Thr Tyr Thr Tyr Gly Asp
            20                  25                  30

Gly Leu Ser Met Ala Glu Leu Ile Asp Ser Arg Gln His Gly Gly Leu
        35                  40                  45

Thr Tyr Asn Asp Phe Leu Val Leu Pro Gly Phe Ile Asn Phe Ala Ala
    50                  55                  60

Ser Asp Val Ser Leu Arg Thr Lys Val Thr Lys Asn Val Thr Leu Asn
65                  70                  75                  80

Thr Pro Phe Leu Ser Ser Pro Met Asp Thr Val Thr Glu Thr Glu Met
                85                  90                  95

Ala Ile Ala Met Gly Leu Met Gly Gly Met Gly Val Ile His Asn Asn
            100                 105                 110

Met Ser Pro Gln Glu Gln Ala Ser Val Val Arg Lys Val Lys Lys Tyr
        115                 120                 125

Glu Asn Gly Phe Ile Thr Glu Pro Leu Cys Leu Asp Pro Lys Ala Thr
    130                 135                 140

Val Gly Asp Val Leu Asp Val Lys Glu Arg Leu Gly Phe Gly Gly Ile
145                 150                 155                 160

Pro Ile Thr Asp Thr Gly Ala Met His Gly Lys Leu Leu Gly Ile Val
                165                 170                 175

Thr Ala Arg Asp Val Gln Phe Arg Asp Thr Thr Leu Pro Leu Ser Glu
            180                 185                 190

Val Met Thr Thr Asp Leu Val Thr Ala Lys Gln Gly Val Thr Leu Glu
        195                 200                 205

Gln Ala Asn Thr Ile Leu Arg Asp Ser Lys Lys Gly Lys Leu Pro Ile
    210                 215                 220

Val Asp Ala Glu Gly Arg Leu Val Ala Leu Ala Arg Ser Asp Leu
225                 230                 235                 240

Leu Lys Asn Gln Asn Phe Pro Leu Ala Ser Lys Arg Pro Glu Ser Lys
                245                 250                 255

Gln Leu Tyr Cys Ala Ala Ala Ile Gly Thr Arg Pro Ser Asp Arg Glu
            260                 265                 270

Arg Leu Ser Leu Leu Val Glu Ala Gly Leu Asp Val Val Ile Leu Asp
        275                 280                 285

Ser Ser Gln Gly Asn Ser Val Tyr Gln Ile Glu Met Ile Gln Trp Ile
    290                 295                 300

Lys Gln Thr Tyr Pro Gln Ile Asp Val Val Ala Gly Asn Val Val Thr
305                 310                 315                 320

Arg Glu Gln Ala Ala Ser Leu Ile Ala Ala Gly Ala Asp Ala Leu Arg
                325                 330                 335

Val Gly Met Gly Ser Gly Ser Ile Cys Ile Thr Gln Glu Val Met Ala
            340                 345                 350

Val Gly Arg Pro Gln Gly Thr Ala Val His Ala Val Ala Glu Phe Ala
```

-continued

```
                355                 360                 365
Ser Lys Phe Gly Val Pro Val Ile Ala Asp Gly Ile Ser Asn Val
    370                 375                 380

Gly His Ile Ala Lys Ala Leu Ala Leu Gly Ala Ser Ala Val Met Met
385                 390                 395                 400

Gly Gly Leu Leu Ala Gly Thr Asn Glu Ser Pro Gly Asp Tyr Phe Tyr
            405                 410                 415

Arg Asp Gly Lys Arg Leu Lys Gly Tyr Arg Gly Met Gly Ser Ile Glu
            420                 425                 430

Ala Met Glu His Gln Lys Lys Gly Lys Ile Ala Gly Ala Thr Gly Lys
            435                 440                 445

Gly Ala Ala Lys Ala Asp Lys Val Ala Thr Asp Glu Asn Ala Ala Thr
    450                 455                 460

Gln Arg Tyr Phe Ser Glu Ser Asp Ala Val Lys Val Ala Gln Gly Val
465                 470                 475                 480

Ala Gly Ala Val Gln Asp Lys Gly Ser Val Lys Lys Phe Leu Pro Tyr
            485                 490                 495

Leu Tyr Thr Gly Leu Gln His Ser Leu Gln Asp Met Gly Val Pro His
            500                 505                 510

Leu Tyr Gln Leu Arg Ser Ala Val Ala Ser Gly Gln Val Arg Phe Glu
            515                 520                 525

Leu Arg Thr Ala Ser Ala Gln Val Glu Gly Gly Val His Gly Leu His
            530                 535                 540

Ser Tyr Glu Lys Arg Leu Phe Ser Ser
545                 550

<210> SEQ ID NO 5
<211> LENGTH: 26
<212> TYPE: DNA
<213> ORGANISM: artificial sequence
<220> FEATURE:
<223> OTHER INFORMATION: The artificial sequence comprises an
      oligonucleotide primer complementary to Ustilago maydis DNA.

<400> SEQUENCE: 5
agatatccct gctagcaacg gtattc                                              26

<210> SEQ ID NO 6
<211> LENGTH: 28
<212> TYPE: DNA
<213> ORGANISM: artificial sequence
<220> FEATURE:
<223> OTHER INFORMATION: The artificial sequence comprises an
      oligonucleotide primer complementary to Ustilago maydis DNA.

<400> SEQUENCE: 6
cgcagacaag agaagcatcc gccggcga                                            28
```

POLYPEPTIDES FOR IDENTIFYING FUNGICIDALLY ACTIVE COMPOUNDS

BACKGROUND OF THE INVENTION

1. Field of the Invention

This invention relates to polypeptides from phytopathogenic fungi with the biological activity of an inosine monophosphate dehydrogenase, to nucleic acids encoding them, to the use of the polypeptides and nucleic acids for identifying modulators of the polypeptides, to methods of identifying such modulators, and to the use of these modulators as fungicides.

2. Description of the Related Art

Undesired fungal growth which leads every year to considerable damage in agriculture can be controlled by the use of fungicides. The demands made on fungicides have increased constantly with regard to their activity, costs and, above all, ecological soundness. There exists therefore a demand for new substances or classes of substances which can be developed into potent and ecologically sound new fungicides. In general, it is customary to search for such new lead structures in greenhouse tests. However, such tests require a high input of labour and a high financial input. The number of the substances which can be tested in the greenhouse is, accordingly, limited. An alternative to such tests is the use of what are known as high-throughput screening (HTS) methods. This involves testing a large number of individual substances with regard to their effect on cells, individual gene products or genes in an automated method. When certain substances are found to have an effect, they can be studied in conventional screening methods and, if appropriate, developed further.

Advantageous targets for fungicides are frequently searched for in essential biosynthetic pathways. Ideal fungicides are, moreover, those substances which inhibit gene products which have a decisive importance in the manifestation of the pathogenicity of a fungus.

Inosine monophosphate dehydrogenase (EC 1.1.1.205), hereinbelow abbreviated to IMP dehydrogenase or IMPDH, catalyses the rate-limiting and irreversible step of de novo GTP synthesis. Inosine 5'-monophosphate (IMP) is reacted with nicotinamide adenine dinucleotide (NAD$^+$) by IMPDH to give NADH/H$^+$ and XMP (FIG. 1). Inosine 5'-monophosphate is the end product of de novo purine biosynthesis and an essential intermediate in the abovementioned synthesis of adenine and guanine nucleotides. Thus, IMPDH is a key enzyme for providing GTP, which is of enormous importance for the cell. GTP is incorporated into RNA and DNA, acts as substrate for GTPases (for example in cellular signal transduction pathways, such as G-protein-coupled receptors), for guanylate cyclase (generation of the secondary messenger substance cGMP) and as cosubstrate in many enzymatic reactions, and plays a role in the post-transcriptional modification of mRNA (5'-cap structure). IMPDH has therefore been a target for some time in the search for antiviral, immunosuppressive, carcinostatic and antimicrobial active compounds.

In addition, there is evidence that IMPDH, in plants, plays yet another, completely different, role which is associated with the assimilation, the transport and the storage of nitrogen. Thus, evidence exists that IMPDH is involved in the formation of ureids and allantoin.

Polypeptides with the activity of an IMPDH have also already been identified in specific fungi. These include the IMPDH from the fungus Candida albicans, which is pathogenic for humans and whose sequence encompasses 521 amino acids. The matching sequence can be obtained for example via what is known as the "trembl" database (U85049, AF249293). The sequences from the filamentous fungi Ashbya gossypii with 522 amino acids (trembl, A94860 and EP 0 927 761 A2), Saccharomyces pombe with 524 AA (Z97211) and Saccharomyces cerevisiae with 524 amino acids (Z46729), which are frequently employed in fermentations, and from the unicellular fungus Pneumocystis carinii, which is pathogenic for humans, with 529 amino acids (AF196975) are likewise available. Interestingly, several genes which encode a polypeptide with the activity of an IMPDH have already been identified in yeast.

Mycophenolic acid, a known specific IMPDH inhibitor, is a known medicament for suppressing the immune response for example following organ transplants. The structure of an IMPDH together with the inhibitor mycophenolic acid has already been elucidated (Sintack et al. (1996) "Structure and Mechanism of Inosine Monophosphate Dehydrogenase in Complex with the Immunosuppressant Mycophenolic Acid". *Cell* 86, 921), and work on the biochemical mechanism of the inhibition of IMPDH by mycophenolic acid exists likewise (Fleming et al. (1996) "Inhibition of IMPDH by Mycophenolic Acid: Dissection of Forward and Reverse Pathways Using Capillary Electrophoresis". *Biochemistry* 35, 6990).

Mycophenolic acid is highly effective against mammalian IMPDH, but markedly less effective as antimicrobial active compound (Digits et al. (1999) "Species Specific Inhibition of Inosine 5'-Monophosphate Dehydrogenase by Mycophenolic Acid". *Biochemistry*, 38 15388). Mycophenolic acid binds to the intermediate which originates when XMP is formed from IMP into the nicotinamide binding pocket of the NAD$^+$ binding site. However, owing to differences of the polypeptides derived from different species, the sensitivity to a human IMPDH is 20 to 450 times greater than to a microbial IMPDH (in this context, see also Zhang et al. (1999) "Differential Signatures of Bacterial and Mammalian IMP Dehydrogenase Enzymes." *Current Medicinal Chemistry* 6, 537).

Further IMPDH inhibitors which are known in the field of medical therapy are, for example, ribovirin, a guanosine analogue, which has antiviral properties, tiazofurin, a C nucleoside which forms an NAD-like tiazofurin adenine dinucleotide following phosphorylation of the 5'-hydroxyl group and which is used as carcinostatic, or mizoribine, which is employed for immunosuppression in transplantation medicine (Goldstein and Colby (1999) "IMP Dehydrogenase: Structural Aspects of Inhibitor Binding". *Current Medicinal Chemistry* 6, 519). In contrast, mizoribine is virtually ineffective against the fungus *C. albicans*, which is pathogenic for humans, and can apparently not be used at all as active substance against candidiasis (Ishikawa (1999) "Mizoribine and Mycophenolate Mofetil". *Current Medicinal Chemistry* 6, 575).

The IMPDH sequence which has been isolated from *C. albicans* shows marked sequence similarity with the IMPDH from *S. cerevisiae* and other ogranisms. The ORF (open reading frame) of the *C. albicans* gene is interrupted by a small intron (289 base pairs (bp)) with typical exon-intron borders (Kohler et al. (1997) Overexpression of a cloned IMP dehydrogenase gene of *Candida albicans* confers resistance to the specific inhibitor mycophenolic acid. *J. Bacteriol.* 179, 2331). The growth of *C. albicans* cells can be inhibited by 1 µg/ml mycophenolic acid, while those cells which have a plasmid with recombinant IMPDH are resistant to up to 40 µg/ml.

In the case of *Pneumocystis carinii*, it has been shown that mycophenolic acid can act as an inhibitor of the IMPDH from this organism (O'Gara et al. (1997) "IMP dehydrogenase from *Pneumocystis carinii* as a potential target". *Antimicrob. Agents Chemother.* 41, 40), and the exploitation of IMPDH as sensitive target of this organism has been proposed. The *Pneumocystis carinii* IMPDH (amino acid sequence) shows homology with bacterial IMPDH (31 to 38%), protozoal IMPDH (48 to 59%), mammalian IMPDH (60 to 62%) and fungal IMPDH (62%). A concentration of 25 µM mycophenolic acid resulted in 50% inhibition of the activity of the recombinant IMPDH.

Earlier work has shown that, as described above while mycophenolic acid inhibits in vitro the growth of some fungi which are pathogenic for humans (for example *C. albicans, Cryptococcus neoformans*), the compound is ineffective against *Candida guilliermondii, Candida krusei, Candida pseudotropicalis, Hansenula anomala* and also ineffective against *S. cerevisiae* (Noto et al. (1969) "Biological properties of mycophenolic acid". J. Antibiot. (Tokyo), 22, 165).

These results show that mammalian IMPDH can be inhibited effectively with the known inhibitor mycophenolic acid, while the effect of the inhibitor is poor in the case of microorganisms. In the case of the fungi which are pathogenic to humans and which have been tested, the effect seems to be variable. Some fungi such as, for example, *S. cerevisiae*, have been described as being not sensitive to inhibition by an IMPDH inhibitor, while an effect, albeit a fungistatic rather than a fungicidal effect, can be observed in other fungi which are pathogenic for humans. The suitability of IMPDH as target protein for fungicides or for use in the search of fungicidal active compounds is therefore doubtful. In particular, an at least fungistatic effect has only been shown as yet in a few fungi which are pathogenic for humans, while no nucleic acid or amino acid sequence of an IMPDH from phytopathogenic fungi has been available as yet, and no results exist on whether phytopathogenic fungi might react sensitively to an IMPDH inhibitor so that such inhibitors can be used as fungicides.

SUMMARY OF THE INVENTION

It is therefore an aim of the present invention to identify, and make available, a suitable new target for potential fungicidal active compounds and to provide a method which makes possible the identification of modulators of this target which can be used as fungicides.

It is therefore in particular an object of the present invention to provide an IMPDH of a phytopathogenic fungus and methods which are suitable for identifying inhibitors of the enzyme and for testing whether such inhibitors can be used as fungicides in phytopathogenic fungi.

In one embodiment, the present invention is directed to a method of identifying fungicides characterized in that
  (a) a polypeptide with the biological activity of an IMP dehydrogenase is brought into contact with a chemical compound or a mixture of chemical compounds,
  (b) the biological activity of the IMP dehydrogenase in the presence of the chemical compound or the mixture of chemical compounds is compared with the biological activity of the IMP dehydrogenase in the absence of the chemical compound or the mixture of chemical compounds, and
  (c) the chemical compound which specifically inhibits the biological activity of the IMP dehydrogenase is determined.

The present invention is also directed to the the use of a polypeptide with the biological activity of an IMP dehydrogenase for finding fungicidal compounds, the use of an inhibitor of a polypeptide with the biological activity of an IMP dehydrogenase as a fungicide and for controlling phytopathogenic fungi and to fungicides which can be identified by the method.

The present invention is also directed to a nucleic acid encoding a polypeptide from phytopathogenic fungide with the biological activity of an IMP dehydrogenase, to DNA constructs encompasing such nucleic acid, to vectors encompassing such nucleic acid, and to host cells containing such nucleic acid.

The present invention is also directed to polypeptides from phytopathogenic fungi with the biological activity of an IMP dehydrogenase which is encoded by the aforementioned nucleic acid and to an antibody which binds specifically to such a polypeptide.

The present invention is also directed to a method of generating the aforementioned nucleic acid by a
  (a) full chemical synthesis, or
  (b) chemical synthesis of oligonucleotides, labelling the oligonucleotides, hybridizing the oligonucleotides with DNA of a genomic library or a cDNA library generated from genomic DNA or mRNA from fungal cells, selecting positive clones, and isolating the hybridizing DNA from positive clones, or
  (c) chemical synthesis of oligonucleotides and amplification of the target DNA by means of PCR.

The present invention is also directed to a method of generating the polypeptide, which includes the steps of
  (a) culturing a host cell according under conditions which ensure the expression of the nucleic acid, or
  (b) expressing the nucleic acid in an in-vitro system, and
  (c) recovering the polypeptide from the cell, the culture medium or the in-vitro system.

The present invention is also directed to a method of finding a compound which modifies the expression of the aforementioned polypeptides of the present invention which includes the steps of
  (a) bringing a host cell containing the nucleic acid of the present invention into contact with a chemical compound or a mixture of chemical compounds,
  (b) determining the polypeptide concentration, and
  (c) determining the chemical compound which specifically influences the expression of the polypeptide.

DESCRIPTION OF THE FIGURES AND OF THE SEQUENCE LISTING

FIG. 1: FIG. 1 is an illustration of the reaction catalysed by IMPDH, which is the conversion of inosine 5'-monophosphate (IMP) to xanthosine 5'-monophosphate (XMP), NADH being produced from $NAD^+$. This reaction, which is catalysed by IMPDH, describes its biological, or enzymatic, activity.

Figure 2:
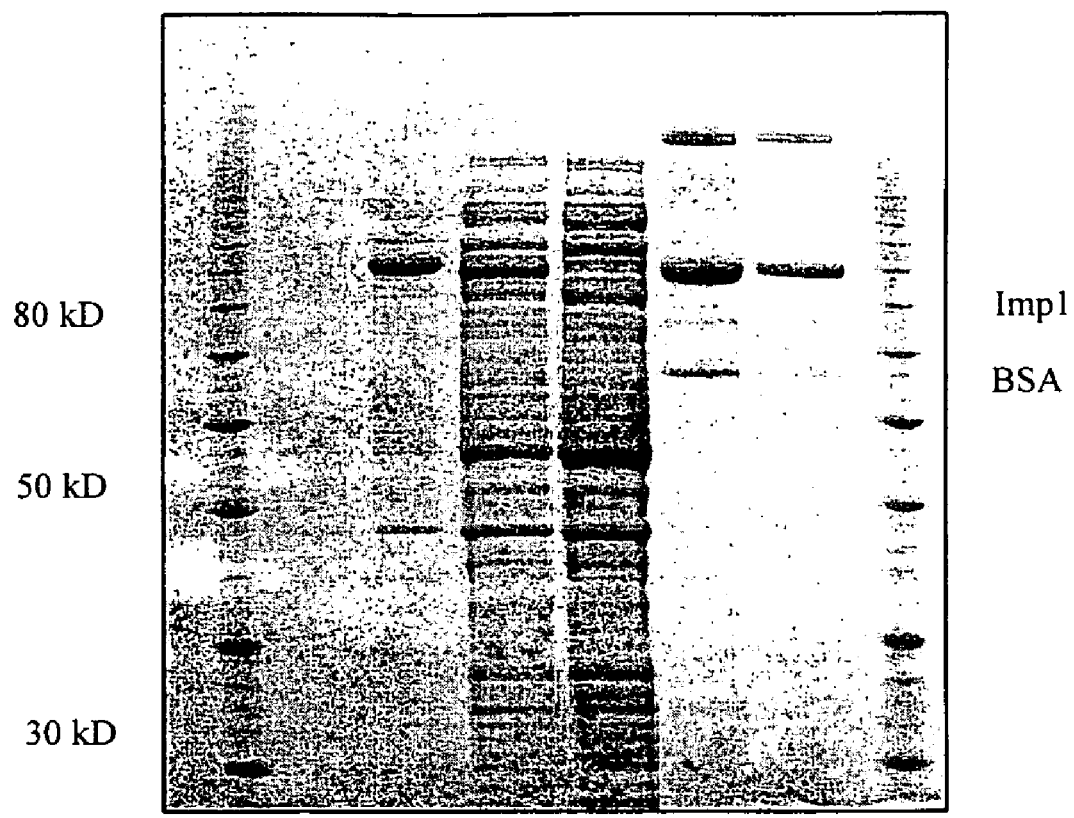

FIG. 2: FIG. 2 demonstrates the purification of IMPDH from *U. maydis* with the aid of a separation in a gel. Lane 1: 10 kD ladder; lane 2: protein extract of an uninduced culture; lane 3: protein extract of an induced culture after incubation for 1.5 h; lane 4: soluble supernatant of the *E. coli* protein extract; lane 5: through-flow of the Ni-NTA columns; lane 6: eluate 1 of the Ni-NTA column; lane 7: eluate 2 of the Ni-NTA column; lane 8: 10 kD ladder.

Figure 3:
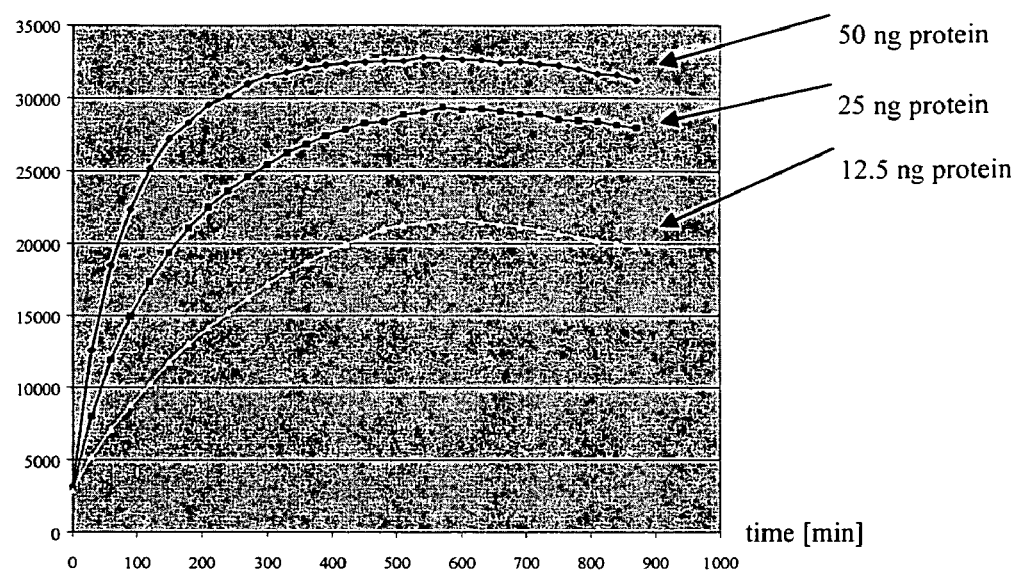

FIG. 3: FIG. 3 is a plot of relative fluoresence versus time for various concentrations of protein illustrating the kinetics of the conversion of $NAD^+$ by IMPDH. 25 µM $NAD^+$ and 50 μM IMP were employed in an assay volume of 50 μl. The protein concentrations used can be seen in the figure. The conversion was monitored with reference to the fluorescence of the NADH produced.

Figure 4:
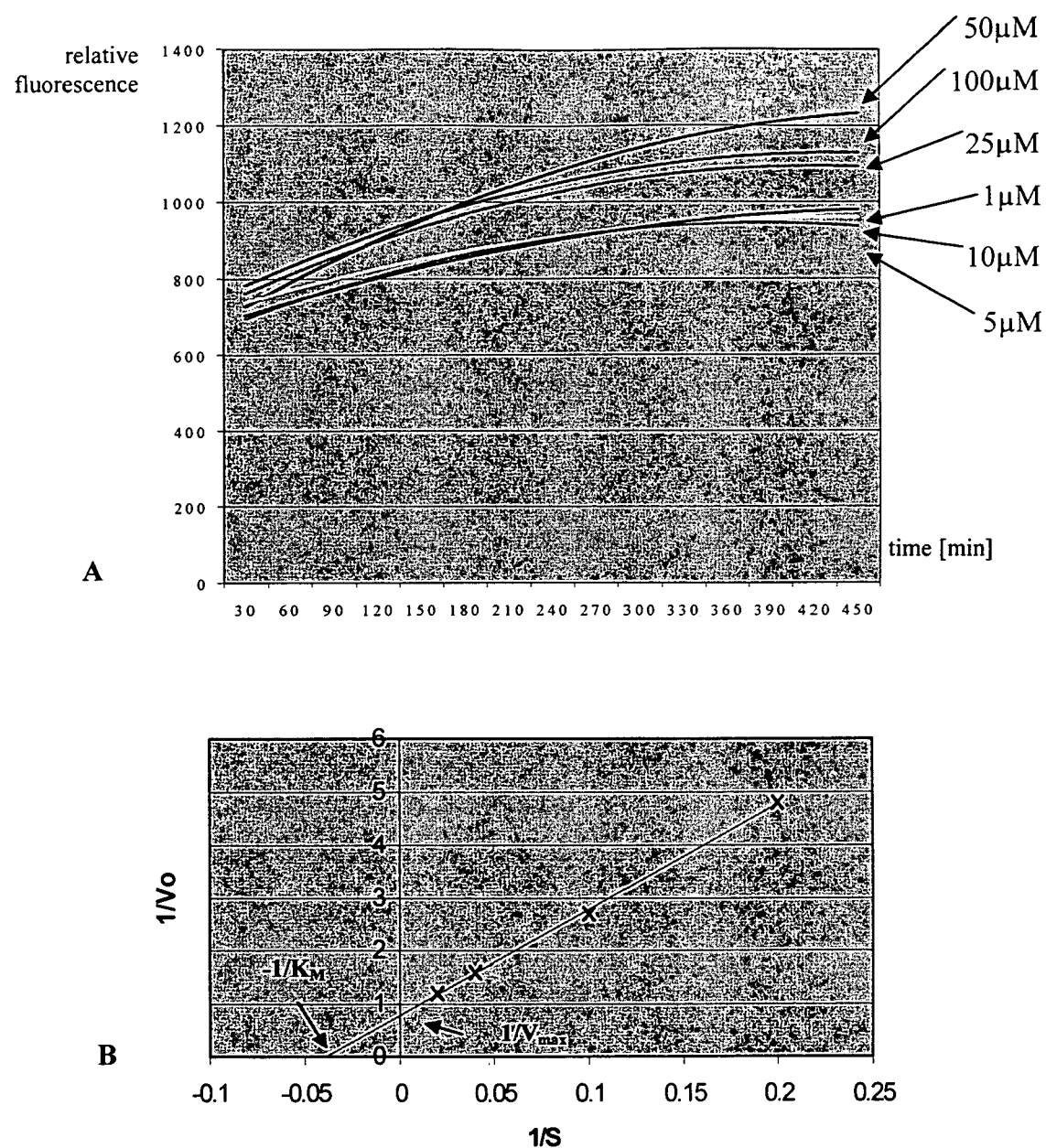

FIG. 4: FIG. 4A is a plot of relative fluoresence versus time. FIG. 4B is a plot of $K_M$ determination for NAD$^+$ with $V_{o/max}$=initial/maximum conversion rate in $\mu M/(mg^{-1} min^{-1})$ and S=substrate concentration in μM.

FIG. 5: FIG. 5 is the sequence alignment at the amino acid level between the *U. maydis* IMP dehydrogenase, the sequences known from *S. cerevisiae*, and the IMP dehydrogenase from *Homo sapiens* and *A. thaliana*. The consensus sequence in the catalytic centre of the enzyme which is typical of IMP dehydrogenases is shown in bold.

SEQ ID NO: 1: Genomic DNA encoding *Ustilago maydis* IMP dehydrogenase. The genomic DNA contains an intron.

SEQ ID NO: 2: Polypeptide sequence encoded by the DNA as shown in SEQ ID NO: 1.

SEQ ID NO: 3: cDNA encoding *Ustilago maydis* IMP dehydrogenase.

SEQ ID NO: 4: Polypeptide sequence encoded by the DNA of SEQ ID NO: 3.

SEQ ID NO: 5: Artificial sequence (primer) suitable for obtaining and/or amplifying the DNA of SEQ ID NO: 1 and 3, and of homologous sequences.

SEQ ID NO: 6: Artificial sequence (primer) suitable for obtaining and/or amplifying the DNA of SEQ ID NO: 1 and 3, and of homologous sequences.

Definitions

The term "identity" as used in the present context refers to the number of sequence positions that are identical in an alignment. In most cases, it is indicated as a percentage of the alignment length.

The term "similarity" as used in the present context, in contrast, assumes the existence of a similarity metric, that is to say a measure for the desired assumed similarity, for example, between a valine and a threonine or a leucine.

The term "homology" as used in the present context, in turn, indicates evolutionary relationship. Two homologous proteins have developed from a shared precursor sequence. The term is not necessarily about identity or similarity, apart from the fact that homologous sequences usually have a higher degree of similarity (or occupy more identical positions in an alignment) than non-homologous sequences.

The term "IMPDH" as used in the present context represents IMP dehydrogenase, also termed inosine 5'-phosphate dehydrogenase, inosinate dehydrogenase, inosine 5'-monophosphate dehydrogenase, inosine monophosphate dehydrogenase, IMP oxidoreductase or inosine monophosphate oxidoreductase, and which catalyses the reaction inosine 5'-monophosphate+NAD$^+$+H$_2$O=xanthosine 5'-monophosphate+NADH/H$^+$.

The term "complete IMPDH" as used in the present context describes the IMPDH encoded by the complete coding region of a transcription unit, starting with the ATG start codon and comprising all the information-bearing exon regions of the gene encoding IMPDH which is present in the source organism, as well as the signals required for correct transcriptional termination.

The term "biological activity of an IMPDH" as used in the present context refers to the ability of a polypeptide to catalyse the above-described reaction, i.e. the conversion of IMP into XMP with simultaneous conversion of NAD$^+$ into NADH.

The term "active fragment" as used in the present context describes nucleic acids encoding IMPDH which are no longer complete, but still encode polypeptides with the biological activity of a IMPDH and which are capable of catalysing a reaction characteristic of IMPDH, as described above. Such fragments are shorter than the above-described complete nucleic acids encoding IMPDH. In this context, nucleic acids may have been removed both at the 3' and/or 5' ends of the sequence, or else parts of the sequence which do not have a decisive adverse effect on the biological activity of IMPDH may have been deleted, i.e. removed. A lower or else, if appropriate, an increased activity which still allows the characterization or use of the resulting IMPDH fragment is considered as sufficient for the purposes of the term as used herein. The term "active fragment" may likewise refer to the amino acid sequence of IMPDH; in this case, it applies analogously to what has been said above for those polypeptides which no longer contain certain portions in comparison with the above-described complete sequence, but where no decisive adverse effect is exerted on the biological activity of the enzyme. The fragments may differ with regard to their length, for example they may have at least 120, at least 300, at least 400 or at least 500 amino acids.

The term "gene" as used in the present context is the name for a segment from the genome of a cell which is responsible for the synthesis of a polypeptide chain.

The term "cDNA" as used in the present context describes complementary DNA obtained from an mRNA by reverse transcription. It only contains the sequences which correspond to the exons of the genomic DNA. Following cDNA sequencing, the amino acid sequence of the protein encoded by it can be deduced, if desired. After introduction of a cDNA into a cell, large amounts of the respective protein encoded by it can be synthesized.

The term "to hybridize" as used in the present context describes the process in which a single-stranded nucleic acid molecule undergoes base pairing with a complementary strand. For example, starting from the sequence information which is mentioned herein or which can be deduced, DNA fragments can be isolated, in this manner, from phytopathogenic fungi other than *Ustilago maydis*, which fragments encode IMPDHs with the same properties as or similar properties to one of the IMPDHs according to the invention.

Hybridization conditions are calculated approximately by the following formula:

The melting temperature $$Tm=81.5° C.+16.6\{\log[c(Na^+)]\}+0.41(\% G+C)-(500/n)$$

(Lottspeich, F., Zorbas H. (ed.). (1998). Bioanalytik. Spektrum Akademischer Verlag, Heidelberg, Berlin).

In this formula, c is the concentration and n the length of the hybridizing sequence segment in base pairs. For a sequence >100 bp, the term 500/n is dropped. The highest stringency involves washing at a temperature of 5–15° C. below Tm and an ionic strength of 15 mM Na$^+$ (corresponds to 0.1×SSC). If an RNA sample is used for hybridization, the melting point is 10–15° C. higher.

Preferred hybridization conditions are stated hereinbelow:

Hybridization solution: DIG Easy Hyb (Roche, ZZ) hydridization temperature: 42° C. to 70° C., preferably at 42–65° C. (DNA-DNA) or 50° C. (DNA-RNA). Stringent temperatures for the hybridization which are particularly suitable in the present case are between 50 and 65° C., a temperature of 65° C. being an especially suitable stringent temperature.

| | |
|---|---|
| Wash step 1: | 2 × SSC, 0.1% SDS 2 × 5 min at room temperature; |
| Wash step 2: | 1 × SSC, 0.1% SDS 2 × 15 min at 50° C.; preferably 0.5 × SSC, 0.1% SDS 2 × 15 min at 65° C.; particularly preferably 0.2 × SSC, 2 × 15 min at 68° C. |

The degree of identity of the nucleic acids is preferably determined with the aid of the program NCBI BLASTN Version 2.0.4. (Altschul et al. (1997) "Gapped BLAST and PSI-BLAST: a new generation of protein database search programs", Nucleic Acids Res. 25:3389).

The term "fungicide" or "fungicidal" as used in the present context refers to chemical compounds which are capable of controlling those fungi which attack and damage plants, plant parts or plant products or reduce their yield or value. The abovementioned plant parts include, for example, leaves, seeds and fruits (such as, for example, berries, fruit, cereal kernels). The abovementioned plant products include plant-derived raw materials or substances such as, for example, timber or fibres.

The term "heterologous promoter" as used in the present context refers to a promoter which has properties other than the promoter which controls the expression of the gene in question in the original organism.

The term "competitor" as used in the present context refers to the property of the compounds to compete with other, possibly yet to be identified, compounds for binding to IMPDH and to displace the latter, or to be displaced by the latter, from the enzyme.

The term "agonist" as used in the present context refers to a molecule which accelerates or increases the IMPDH activity.

The term "antagonist" as used in the present context refers to a molecule which slows down or prevents the IMPDH activity.

The term "modulator" as used in the present context is the generic term for agonist or antagonist. Modulators can be small organochemical molecules, peptides or antibodies which bind to the polypeptides according to the invention or influence their activity. Moreover, modulators can be small organochemical molecules, peptides or antibodies which bind to a molecule which, in turn, binds to the polypeptides according to the invention, thus influencing their biological activity. Modulators can be natural substrates and ligands, or structural or functional mimetics of these. However, the term "modulator" as used in the present context takes the form of those molecules which do not constitute the natural substrates or ligands.

The term "inhibitor" or "specific inhibitor" as used in the present context refers to a substance which directly or indirectly inhibits at least one, but also, if appropriate, more of the abovementioned enzymatic activities. Such an inhibitor is preferably specific, i.e. it inhibits the IMPDH activity at a concentration which is lower than the concentration of an inhibitor required for causing another unrelated effect. Preferably the concentration is lower by a factor of two, more preferably by a factor of five and most preferably by a factor of at least ten or 20 than the concentration of a compound required for causing an unspecific effect.

DETAILED DESCRIPTION OF THE INVENTION

Within the scope of the present invention, the nucleic acid sequence encoding the IMPDH from the phytopathogenic fungus U. maydis has been identified and isolated, and the polypeptide encoded by it has been obtained. There has furthermore been developed a method which is suitable for determining the IMPDH activity and for identifying and assessing inhibitors of the enzyme, including in HTS and UHTS methods. It has further been demonstrated within the scope of the present invention that the IMPDH inhibitors from phytopathogenic fungi can be used as plant protection agents.

The smut fungus Ustilago maydis, a Basidiomycete, attacks maize plants. The disease occurs in all areas where maize is grown, but gains importance only during dry years. Typical symptoms are the gall-like, fist-sized swellings (blisters) which are formed on all aerial plant parts. The galls are first covered by a whitish-grey coarse membrane. When the membrane ruptures, a black mass of ustilospores, which is first greasy and later powdery, is released. Further species of the genus Ustilago are, for example, U. nuda (causes loose smut of barley and wheat), U. nigra (causes black smut of barley), U. hordei (causes covered smut of barley) and U. avenae (causes loose smut of oats).

The U. maydis IMPDH (hereinbelow termed "Imp1") extends over 1999 bp. The coding cDNA is 1659 bp in length. Accordingly, Imp1 contains an intron 340 bp in length. The polypeptide deduced from the ORF of the cDNA is 553 amino acids in length. This corresponds to a calculated molecular weight of approximately 60 kD for the monomer.

The nucleic acid sequence encoding Imp1 is disclosed in the present application as SEQ ID NO: 1 (genomic sequence) or SEQ ID NO: 3 (cDNA). The polypeptides encoded by each of them are deposited in the present application as SEQ ID NO: 2 and SEQ ID NO: 4.

The present invention thus completely describes for the first time an IMPDH of a phytopathogenic fungi, in this case Ustilago maydis. In addition to the IMPDH from Saccharomyces cerevisiae, Saccharomyces pombe, Candida albicans, C. neoformans and Pneumocystis carinii, which have been described above, no sequences encoding an IMPDH are known to date from other fungi. The IMPDH-encoding sequence from a phytopathogenic Basidiomycete, in particular, was previously unknown.

A homology comparison of the U. maydis sequence encoding IMPDH as shown in SEQ ID NO: 1 and 3 with known IMPDH-encoding sequences from other fungi, the human sequence and the A. thaliana sequence reveals that the S. cerevisiae sequence shows the highest degree of homology with the U. maydis sequence (Table I). This is of particular interest since mycophenolic acid, which has been described above and which is a known inhibitor of human IMPDH and still acts fungistatically in C. albicans has no effect in the case of S. cerevisiae (Noto et al. (1969) "Biological properties of mycophenolic acid". J. Antibiot. (Tokyo), 22, 165). Table I lists the homology of DNA encoding IMPDH from various organisms in comparison with the DNA encoding U. maydis IMPDH.

TABLE I

| Organism | Homology in % |
|---|---|
| P. carinii | 59 |
| C. neoformans | 55 |
| C. albicans | 59 |
| S. cerevisiae(imh1) | 60 |
| S. cerevisiae(imh2) | 63 |
| S. cerevisiae(imh3) | 64 |
| H. sapiens | 59 |
| A. thaliana | 43 |

By means of knock-out analyses in the *Basidiomycete Ustilago maydis* it has, surprisingly, been found within the scope of the present invention that the enzyme in this phytopathogenic fungus is important for the survival of the organism. This allows the conclusion that IMPDH plays an important role for phytopathogenic fungi, or fungi in general. However, similar results have not been demonstrated in fungi as yet, not even in *S. cerevisiae*, which might be contributory to the fact that several IMPDH-encoding genes exist in yeast and the role of IMPDH was therefore not recognized. Thus, IMPDH was recognized for the first time as an optimum target for the search for new, specific fungicides against phytopathogenic fungi. It is therefore possible to identify, with the aid of this target, lead structures which may be entirely new and which inhibit IMPDH and can be used as crop protection agents or fungicides.

It has furthermore been found within the scope of the present invention that IMPDH can be used for identifying substances in suitable test methods which affect the activity of the enzyme, which is not necessarily the case in various targets which are theoretically of interest. In addition to an IMPDH from a phytopathogenic fungus which is characterized by its amino acid sequence and the nucleic acid sequence encoding it, suitable test methods for identifying modulators of the enzyme and which are also suitable for use in HTS methods are thus provided.

It has furthermore been found within the scope of the present invention that IMPDH is indeed inhibited in vitro by active compounds and that a fungal organism treated with these active compounds can be damaged or killed by the treatment with these active compounds. IMPDH inhibitors from phytopathogenic fungi can thus be used as fungicides in crop protection. For example, it is shown in the present invention that the inhibition of IMPDH with substances identified in an abovementioned test system leads to destruction of the treated fungi both in synthetic media and on the plant.

As has already been explained above, it was previously unknown that IMPDH, in fungi, can be a target protein of fungicidally active substances, despite the intense research into IMPDHs and despite the IMPDH inhibitors which were already known and employed in human medicine. Thus, it is demonstrated for the first time in the present invention that IMPDH constitutes an enzyme which is important in particular for phytopathogenic fungi, and which is therefore particularly suitable for being used as target protein for the search for further, improved fungicidally active compounds.

IMPDH can be divided into several homologous regions. One of these regions concentrates on the catalytic centre, in particular on a cysteine, which probably plays a role in IMP binding. This centre is a sequence motif which is characteristic for IMP dehydrogenases. Such a motif was identified by a suitable search in the PROSITE database (Hofnann K., Bucher P., Falquet L., Bairoch A. (1999) "The PROSITE database, its status in 1999". *Nucleic Acids Res.* 27, 215). This can be shown as follows:

[LIVM]-[RK]-[LIVM]-G-[LIVM]-G-x-G-S-[LIVM]-C-x-T,

PROSITE allows the identification of functional domains of IMP dehydrogenases and is suitable for predicting the function of a gene product.

The Prosite motif is shown using the one-letter code. The symbol "x" represents a position at which any amino acid is accepted. A variable position at which various specific amino acids are accepted is shown in square brackets "[ . . . ]", the amino acids which are possible at this position being enumerated. Amino acids which are not accepted at a specific position, in contrast, are shown in curly brackets "{ . . . }". A hyphen "-" separates the individual elements or positions of the motif. If a specific position is repeated, for example "x" several times in succession, this can be shown by showing the number of repetitions within brackets after the x, for example "x (3)", which represents "x-x-x".

Thus, a Prosite motif ultimately represents the components of a consensus sequence and distances between the amino acids involved, and is therefore typical of a particular class of enzymes. With reference to this motif, and based on the nucleic acids according to the invention, further polypeptides from phytopathogenic fungi which belong to the same class as the polypeptide according to the invention can be identified or assigned.

In the case of the *U. maydis* IMPDH, this motif is likewise present in *S. cerevisiae, Homo sapiens* or *Arabidopsis thaliana* (see FIG. 5), the *U. maydis* sequence differing from the *S. cerevisiae* sequence at one or two positions. The specific consensus sequence for an IMP dehydrogenase according to the invention which can be used for identifying or assigning further polypeptides according to the invention is therefore particularly preferably

-LRVGMGSGSICIT-(SEQ ID NO: 7).

The abovementioned Prosite motif, or the specific consensus sequence, are typical of the polypeptides according to the invention which can be defined in terms of structure with reference to these consensus sequences and can thus also be identified unambiguously.

The present invention therefore also relates to polypeptides from phytopathogenic fungi with the biological activity of an IMPDH which encompass the abovementioned Prosite motif [LIVM]-[RK]-[LIVM]-G-[LIVM]-G-x-G-S-[LIVM]-C-x-T, preferably those polypeptides which encompass the abovementioned consensus sequence -LRVGMGSGSICIT-.

Owing to the above results and the homology which exist in species-specific nucleic acids encoding IMPDH, it is also possible to identify, and use, IMPDHs from other phytopathogenic fungi in order to achieve the above aim, i.e. they can likewise be used for identifying IMPDH inhibitors which, in turn, can be used as fungicides in crop protection. However, it is also feasible to use another fungus which is not phytopathogenic, or its IMPDH or the sequence encoding it, in order to identify fungicidally active IMPDH inhibitors. Owing to the sequence as shown in SEQ ID NO: 1 or SEQ ID NO: 3 shown herein, or the primers shown under SEQ ID NO: 5 and 6, and, if appropriate, using the above-shown consensus sequence or the Prosite motif, it is possible for the skilled worker to obtain and to identify further nucleic acids encoding IMP dehydrogenases from other phytopathogenic fungi, for example by means of PCR. Such nucleic acids and their use in methods for identifying fungicidal active compounds are considered as being encompassed by the present invention.

The present invention therefore relates to nucleic acids which encode complete polypeptides from phytopathogenic fungi with the biological activity of an IMPDH. These nucleic acids preferably have an identity of at least 60%, at least 65%, at least 70%, at least 75%, at least 80%, at least 85%, at least 90%, at least 95% and in particular at least 98% over a length of 60, 300, 600 or 1200 base pairs and preferably over the entire length of the coding sequence. The abovementioned nucleic acids in each case preferably encompass the abovementioned Prosite motif or the abovementioned consensus sequence.

The present invention particularly relates to nucleic acids which encode IMPDHs from phytopathogenic *Basidiomycetes*, preferably from the genus *Ustilago*. *The present invention very particularly preferably relates to nucleic acids which encode the Ustilago maydis IMPDH.*

The present invention especially preferably relates to nucleic acids from *Ustilago maydis* which encode a polypeptide as shown in SEQ ID NO: 2 or SEQ ID NO: 4 or active fragments thereof. The present invention relates especially to the nucleic acids as shown in SEQ ID NO: 1 and SEQ ID NO: 3.

The nucleic acids according to the invention especially take the form of single-stranded or double-stranded deoxyribunucleic acids (DNA) or ribonucleic acids (RNA). Preferred embodiments are fragments of genomic DNA, which may contain introns, and cDNAs.

The nucleic acids according to the invention preferably take the form of DNA fragments which correspond to the cDNA of the nucleic acids according to the invention.

The nucleic acids according to the invention particularly preferably encompass a sequence from phytopathogenic fungi encoding a polypeptide with the biological activity of an IMPDH selected from
   a) the sequence as shown in SEQ ID NO: 1 or SEQ ID NO: 3
   b) sequences which encode a polypeptide encompassing the amino acid sequence as shown in SEQ ID NO: 2 or SEQ ID NO: 4,
   c) sequences which encode a polypeptide encompassing the motif [LIVM]-[RK]-[LIVM]-G-[LIVM]-G-x-G-S-[LIVM]-C-x-T or the consensus sequence -LRVG-MGSGSICIT-,
   d) part-sequences of the sequences defined under a) to c) which are at least 15 base pairs in length,
   e) sequences which hybridize with the sequences defined under a) to c) at a hybridization temperature of 42–65° C.,
   f) sequences with at least 60%, preferably 80%, particularly preferably 90% and very particularly preferably 95% identity with the sequences defined under a) to c),
   g) sequences which are complementary to the sequences defined under a) to f), and
   h) sequences which, owing to the degeneracy of the genetic code, encode the same amino acid sequence as the sequences defined under a) to c).

The nucleic acids according to the invention can be generated in the customary manner. For example, the nucleic acid molecules can be generated exclusively by chemical synthesis. However, it is also possible to synthesize chemically short sections of the nucleic acids of the invention, such as, for example, the oligonucleotides as shown in SEQ ID NO: 5 and 6, and such oligonucleotides can be radiolabelled or labelled with a fluorescent dye. The labelled oligonucleotides can also be used for screening cDNA libraries generated starting from mRNA, for example, from phytopathogenic fungi. Clones with which the labelled oligonucleotides hybridize are selected for isolating the DNA fragments in question. After characterization of the DNA which has been isolated, the nucleic acids according to the invention are obtained in a simple manner.

Alternatively, the nucleic acids according to the invention can also be generated by means of PCR methods using chemically synthesized oligonucleotides.

The term "oligonucleotide(s)" as used in the present context refers to DNA molecules composed of 10 to 50 nucleotides, preferably 15 to 30 nucleotides. They are synthesized chemically and can be used as probes for hybridization experiments or as primers for PCR (polymerase chain reaction).

To prepare the polypeptides according to the invention, in particular the polypeptide encoded by the nucleic acid sequence as shown in SEQ ID NO: 1 or SEQ ID NO: 3, it is furthermore possible to culture host cells containing at least one of the nucleic acids according to the invention under suitable conditions. Thereafter, the desired polypeptides can be isolated in the customary manner from the cells or the culture medium. The polypeptides can also be prepared in in-vitro systems.

To prepare the *Ustilago maydis* IMPDH according to the invention, it is possible, for example, to express the gene recombinantly in *Escherichia coli* and to prepare an enzyme preparation from *E. coli* cells.

Thus, to express the polypeptide Imp1, which is encoded by imp1, the corresponding ORF was amplified from mRNA by methods known to the skilled worker using gene-specific primers which are deposited in the sequence listing as SEQ ID NO: 5 and SEQ ID NO: 6. The cDNA in question was cloned into the vector pET32a (Novagen, allows the introduction of a His-tag (N- or C-terminal) or of an S-tag). The resulting plasmid p830 contains the complete coding sequence of imp1 in an N-terminal fusion with thioredoxin-tag from the vector. The Imp1 fusion protein has a calculated mass of 78 kD (Example 1 and FIG. 2).

Plasmid p830 was the used for the recombinant expression of Imp1 in *E. coli* cells (Example 1).

As has already been mentioned above for the nucleic acids, the present invention is not only restricted to the sequence as shown in SEQ ID NO: 2 or SEQ ID NO: 4. The results which are shown here for the first time within the scope of the present invention likewise apply to other polypeptides from phytopathogenic fungi with the biological activity of an IMPDH. Thus, it is also possible to obtain, and use in methods according to the invention, homologous IMPDHs from other such species as mentioned above. Polypeptides from phytopathogenic fungi with the biological activity of an IMPDH are therefore considered as being encompassed by the subject-matter of the present invention.

The abovementioned homologous polypeptides particularly preferably take the form of those which have at least 60%, at least 65%, at least 70%, at least 75%, at least 80%, at least 85%, at least 90%, at least 95% and in particular at least 98% similarity with the *Ustilago maydis* IMPDH over a length of at least 20, preferably at least 25, particularly preferably at least 30 and very particularly preferably at least 100 consecutive amino acids and most preferably over the entire length.

Such polypeptides, which are homologous to the *Ustilago maydis* IMPDH, in particular to the polypeptide of SEQ ID NO: 2 or SEQ ID NO: 4 and which can be used for identifying fungicidal active substances, need not constitute complete fungal IMPDHs, but may also only constitute fragments of these as long as they at least still have a biological activity of the complete IMPDH. Polypeptides which exert the same type of biological activity as an IMPDH with an amino acid sequence as shown in SEQ ID NO: 2 or SEQ ID NO: 4 are still considered as being according to the invention. Polypeptides which are considered as according to the invention are, in particular, those polypeptides which correspond to IMPDHs for example of the following phytopathogenic fungi, or to fragments of these, and which still have their biological activity:

*Plasmodiophoromycetes, Oomycetes, Chytridiomycetes, Zygomycetes, Ascomycetes, Basidiomycetes* and *Deuteromycetes*, for example

*Pythium* species such as, for example, *Pythium ultimum, Phytophthora* species such as, for example, *Phytophthora infestans, Pseudoperonospora* species such as, for example, *Pseudoperonospora humuli* or *Pseudoperonospora cubensis, Plasmopara* species such as, for example, *Plasmopara viticola, Bremia* species such as, for example, *Bremia lactucae, Peronospora* species such as, for example, *Peronospora pisi* or *P. brassicae, Erysiphe* species such as, for example, *Erysiphe graminis, Sphaerotheca* species such as, for example, *Sphaerotheca fuliginea, Podosphaera* species such as, for example, *Podosphaera leucotricha, Venturia* species such as, for example, *Venturia inaequalis, Pyrenophora* species such as, for example, *Pyrenophora teres* or *P. graminea* (conidial form: *Drechslera*, syn: *Helminthosporium*), *Cochliobolus* species such as, for example, *Cochliobolus sativus* (conidial form: *Drechslera*, syn: *Helminthosporium*), *Uromyces* species such as, for example, *Uromyces appendiculatus, Puccinia* species such as, for example, *Puccinia recondita, Sclerotinia* species such as, for example, *Sclerotinia sclerotiorum, Tilletia* species such as, for example, *Tilletia caries; Ustilago* species such as, for example, *Ustilago nuda* or *Ustilago avenae, Pellicularia* species such as, for example, *Pellicularia sasakii, Pyricularia* species such as, for example, *Pyricularia oryzae, Fusarium* species such as, for example, *Fusarium culmorum, Botrytis* species, *Septoria* species such as, for example, *Septoria nodorum, Leptosphaeria* species such as, for example, *Leptosphaeria nodorum, Cercospora* species such as, for example, *Cercospora canescens, Alternaria* species such as, for example, *Alternaria brassicae* or *Pseudocercosporella* species such as, for example, *Pseudocercosporella herpotrichoides*.

Others which are of particular interest are, for example, *Magnaporthe grisea, Cochliobulus heterostrophus, Nectria hematococcus* and *Phytophthora* species.

The polypeptides according to the invention thus preferably encompass an amino acid sequence from phytopathogenic fungi selected from:

(a) the sequence as shown in SEQ ID NO: 2 or SEQ ID NO: 4

(b) sequences encompassing the motif [LIVM]-[RK]-[LIVM]-G-[LIVM]-G-x-G-S-[LIVM]-C-x-T or the consensus sequence-LRVGMGSGSICIT-, (c) part-sequences of the sequences defined under a) and b) which are at least 15 amino acids in length, (d) sequences which have at least 60%, preferably 70%, particularly preferably at least 80% and very particularly preferably 90% identity with the sequences defined under a) and b), and (e) sequences which have the same biological activity as the sequences defined under a) and b).

The term "polypeptides" as used in the present context refers not only to short amino acid chains which are generally referred to as peptides, oligopeptides or oligomers, but also to longer amino acid chains which are normally referred to as proteins. It encompasses amino acid chains which can be modified either by natural processes, such as post-translational processing, or by chemical prior-art methods. Such modifications may occur at various sites and repeatedly in a polypeptide, such as, for example, on the peptide backbone, on the amino acid side chain, on the amino and/or the carboxyl terminus. For example, they encompass acetylations, acylations, ADP ribosylations, amidations, covalent linkages to flavins, haem moieties, nucleotides or nucleotide derivatives, lipids or lipid derivatives or phosphatidylinositol, cyclizations, disulphide bridge formations, demethylations, cystine formations, formylations, gamma-carboxylations, glycosylations, hydroxylations, iodinations, methylations, myristoylations, oxidations, proteolytic processings, phosphorylations, selenoylations and tRNA-mediated amino acid additions.

The polypeptides according to the invention may exist in the form of "mature" proteins or as parts of larger proteins, for example as fusion proteins. They can furthermore exhibit secretion or leader sequences, pro-sequences, sequences which allow simple purification, such as polyhistidine residues, or additional stabilizing amino acids. The proteins according to the invention may also exist in the form in which they are naturally present in the source organism, from which they can be obtained directly, for example.

In comparison with the corresponding regions of naturally occurring IMPDHs, the polypeptides according to the invention can have deletions or amino acid substitutions, as long as they still exert at least the biological activity of a complete IMPDH. Conservative substitutions are preferred. Such conservative substitutions encompass variations, one amino acid being replaced by another amino acid from among the following group:

1. Small, aliphatic residues, non-polar residues or residues of little polarity: Ala, Ser, Thr, Pro and Gly;
2. Polar, negatively charged residues and their amides: Asp, Asn, Glu and Gln;
3. Polar, positively charged residues: His, Arg and Lys;
4. Large aliphatic non-polar residues: Met, Leu, Ile, Val and Cys; and
5. Aromatic residues: Phe, Tyr and Trp.

Preferred conservative substitutions can be seen from the following list:

| Original residue | Substitution |
|---|---|
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

One possible IMPDH purification method is based on preparative electrophoresis, FPLC, HPLC (for example using gel filtration columns, reversed-phase columns or mildly hydrophobic columns), gel filtration, differential precipitation, ion-exchange chromatography or affinity chromatography.

A rapid method of isolating the polypeptides according to the invention which are synthesized by host cells using a nucleic acid to be used in accordance with the invention starts with expressing a fusion protein, where the fusion moiety may be purified in a simple manner by affinity purification. For example, the fusion moiety may be a 6×His tag, in which case the fusion protein can be purified on a nickel-NTA affinity column. The fusion moiety can be removed by partial proteolytic cleavage, for example at linkers between the fusion moiety and the polypeptide according to the invention which is to be purified. The linker can be designed in such a way that it includes target amino acids, such as arginine and lysine residues, which define sites for trypsin cleavage. Standard cloning methods using oligonucleotides may be employed for generating such linkers.

Other purification methods which are possible are based, in turn, on preparative electrophoresis, FPLC, HPLC (e.g. using gel filtration columns, reversed-phase columns or mildly hydrophobic columns), gel filtration, differential precipitation, ion-exchange chromatography and affinity chromatography.

The terms "isolation or purification" as used in the present context mean that the polypeptides according to the invention are separated from other proteins or other macromolecules of the cell or of the tissue. The protein content of a composition containing the polypeptides according to the invention is preferably at least 10 times, particularly preferably at least 100 times, higher than in a host cell preparation.

The polypeptides according to the invention may also be affinity-purified without fusion moieties with the aid of antibodies which bind to the polypeptides.

The present application thus also relates to a method for preparing the polypeptide Imp1 with the SEQ ID NO: 2 or SEQ ID NO: 4 or polypeptides which are homologous thereto from phytopathogenic fungi with the activity of an IMPDH, which comprises
(a) culturing a host cell containing at least one expressible nucleic acid sequence encoding a polypeptide from phytopathogenic fungi with the biological activity of an IMPDH under conditions which ensure the expression of this nucleic acid, or
(b) expressing an expressible nucleic acid sequence encoding a polypeptide from phytopathogenic fungi with the biological activity of an IMPDH in an in-vitro system, and
(c) recovering the polypeptide from the cell, the culture medium or the in-vitro system.

In particular, the present invention relates to a method for preparing the polypeptide Imp1 with the SEQ ID NO: 2 or SEQ ID NO: 4 or polypeptides which are homologous thereto with the activity of an IMPDH from phytopathogenic fungi, wherein
(a) an expressible nucleic acid sequence encoding a polypeptide from phytopathogenic fungi with the biological activity of an IMPDH is transformed into suitable host cells,
(b) the transformed cells are incubated at a suitable temperature, 0.2% of glucose being added to the medium,
(c) the cells are induced after a period which is suitable for sufficient growth of the cells,
(d) the cells are harvested after a period suitable for sufficient expression of the nucleic acid stated under (a), and, if appropriate
(e) the polypeptide is isolated from the harvested cells and purified.

The cells thus obtained which contain the polypeptide according to the invention, or the purified polypeptide thus obtained, are suitable for use in methods for identifying IMPDH modulators or inhibitors.

The present invention thus also relates to the use of polypeptides from phytopathogenic fungi which exert at least one biological activity of an IMPDH and which encompass an amino acid sequence selected from the following sequences
(a) the sequence as shown in SEQ ID NO: 2 or SEQ ID NO: 4
(b) sequences encompassing the motif [LIVM]-[RK]-[LIVM]-G-[LIVM]-G-x-G-S-[LIVM]-C-x-T or the consensus sequence -LRVGMGSGSICIT-,
(c) sequences which have at least 60%, preferably 70%, particularly preferably at least 80% and very particularly preferably 90% identity with the sequences defined under a) and b), and
(d) sequences which have the same biological activity as the sequences defined under a) and b)

in methods for identifying inhibitors of a polypeptide from phytopathogenic fungi with the activity of an IMPDH, it being possible to use the IMPDH inhibitors as fungicides.

Particular preference is given to the use of polypeptides from phytopathogenic *Basidiomycetes*, especially from the genus *Ustilago*, in particular from *Ustilago maydis*, the polypeptide as shown in SEQ ID NO: 2 or SEQ ID NO: 4 being particularly preferred, in methods for identifying inhibitors of a polypeptide from phytopathogenic fungi with the activity of an IMPDH, it being possible to use the IMPDH inhibitors as fungicides.

Fungicides which are found with the aid of one of the IMPDHs according to the invention can thus also interact with IMPDHs from other phytopathogenic fungal species, but the interaction with the different IMPDHs which are present in these fungi need not always be equally pronounced. This explains inter alia the selectivity of active substances which has been observed.

As already illustrated above, the use of the nucleic acids or polypeptides according to the invention in a suitable method makes it possible to find compounds which bind to the polypeptides according to the invention and/or which inhibit the compound. They can then be used in plants as fungicides.

The present invention therefore also relates to a method which is suitable for identifying fungicidal active compounds which bind to the polypeptides according to the invention and/or modulate, i.e. activate or inhibit, their biological activity.

Methods which are suitable for identifying modulators, i.e. activators or inhibitors, or agonists or antagonists, of the polypeptides according to the invention are generally based on the determination of the activity or the biological functionality of the polypeptide. Suitable for this purpose are, in principle, methods based on intact cells (in-vivo methods), but also methods which are based on the use of the polypeptide isolated from the cells, which may be present in purified or partially purified form or else as a crude extract. These cell-free in-vitro methods, like in-vivo methods, can be used on a laboratory scale, but preferably also in HTS or UHTS methods.

A large number of assay systems for the purpose of assaying compounds and natural extracts are preferably designed for high throughput numbers in order to maximize the number of substances assayed within a given period. Assay systems based on cell-free processes require purified or semipurified protein. They are suitable for an "initial" assay, which aims mainly at detecting a possible effect of a substance on the target protein. Once such an initial assay has taken place, and one or more compounds, extracts and the like have been found, the effect of such compounds can be studied in the laboratory in a more detailed fashion. Thus, inhibition or activation of the polypeptide according to the invention in vitro can be assayed again as a first step in order to subsequently assay the activity of the compound on the target organism, in this case one or more phytopathogenic fungi. If appropriate, the compound can then be used as starting point for the further search and development of fungicidal compounds which are based on the original structure, but are optimized with regard to, for example, activity, toxicity or selectivity.

To find modulators, for example a synthetic reaction mix (for example in-vitro transcription products) or a cellular component such as a membrane, a compartment or any other preparation containing the polypeptides according to the invention can be incubated together with an optionally labelled substrate or ligand of the polypeptides in the presence and absence of a candidate molecule which can be an agonist or antagonist. The ability of the candidate molecule to increase or to inhibit the activity of the polypeptides according to the invention can be identified for example on the basis of increased or reduced binding of the optionally labelled ligand or increased or reduced conversion of the optionally labelled substrate. Molecules which lead to an increased activity of the polypeptides according to the invention are agonists. Molecules inhibit the biological activity of the polypeptides according to the invention are good antagonists.

Detection of the biological activity of the polypeptides according to the invention can be improved by what is known as a reporter system. In this aspect, reporter systems comprise, but are not restricted to, calorimetrically or fluorimetrically detectable substrates which are converted into a product, or a reporter gene which responds to changes in the activity or the expression of the polypeptides according to the invention, or other known binding assays, A further example of a method by which modulators of the polypeptides according to the invention can be found is a displacement assay in which the polypeptides according to the invention and a potential modulator are combined, under suitable conditions, with a molecule which is known to bind to the polypeptides according to the invention, such as a natural substrate or ligands or a substrate or ligand mimetic. The polypeptides according to the invention can themselves be labelled, for example fluorimetrically or calorimetrically, so that the number of the polypeptides which are bound to a ligand or which have undergone a conversion can be determined accurately. However, binding can likewise be monitored by means of the optionally labelled substrate, ligand or substrate analogue. The efficacy of an agonist or antagonist can be determined in this manner.

Effects such as cell toxicity are, as a rule, ignored in these in-vitro systems. The assay systems check not only inhibitory, or suppressive effects of the substances, but also stimulatory effects. The efficacy of a substance can be checked by concentration-dependent assay series. Control mixtures without test substances can be used for assessing the effects.

Owing to the host cells containing nucleic acids encoding IMPDH according to the invention and available with reference to the present invention, the development of cell-based assay systems for identifying substances which modulate the activity of the polypeptides according to the invention, is made possible.

Thus, yet another possibility of identifying substances which modulate the activity of the polypeptides according to the invention is what is known as the scintillation proximity assay (SPA), see EP 015 473. This assay system exploits the interaction of a polypeptide (for example *U. maydis* IMPDH) with a radiolabelled ligand or substrate. Here, the polypeptide is bound to microspheres or beads which are provided with scintillating molecules. As the radioactivity declines, the scintillating substance in the microsphere is excited by the subatomic particles of the radiolabel, and a detectable photon is emitted. The assay conditions are optimized so that only those particles emitted from the ligand lead to a signal that are emitted by a ligand bound to the polypeptide according to the invention.

The modulators to be identified are preferably small organochemical compounds.

Accordingly, a method for identifying a compound which modulates the activity of an IMPDH from phytopathogenic fungi and which can be used in crop protection as fungicide consists in a) bringing a polypeptide according to the invention or a host cell containing this polypeptide into contact with a chemical compound or a mixture of chemical compounds under conditions which permit the interaction of a chemical compound with the polypeptide, b) comparing the activity of the polypeptide according to the invention in the absence of a chemical compound with the activity of the polypeptide according to the invention in the presence of a chemical compound or a mixture of chemical compounds, and c) determining the chemical compound which specifically modulates the activity of the polypeptide according to the invention.

In this context, the compound which specifically inhibits the activity of the polypeptide according to the invention is particularly preferably determined. The term "activity" as used in the present context refers to the biological activity of the polypeptide according to the invention.

The activity, or the increase or decrease in activity, of the polypeptide according to the invention is preferably determined by means of the conversion of the substrate $NAD^+$ into NADH. Here, the lower, or inhibited, activity of the polypeptide according to the invention is monitored with reference to the photospectrometric determination of the decrease in $NAD^+$ or the increase in NADH. This is because, owing to the fact that the nicotinamide ring absorbs light, the reduced nicotinamide coenzyme NADH has an absorption maximum at 340 nm. In contrast, the oxidized form $NAD^+$ does not absorb between 300 and 400 nm. The enzyme reaction according to the invention which leads to the $NAD^+$ being reduced can therefore be monitored with reference to the increase in absorption, for example at 340 nm. The effect of an inhibitor on the reaction can thus be determined using this method.

A further possibility of determining the activity, or the decrease or increase in activity, by means of the conversion of the substrate $NAD^+$ into NADH is to detect the NADH formed in a coupled luciferase assay. Here, the reaction is coupled with NADH-FMN oxidoreductase as outlined hereinbelow:

$FMNH_2+RCHO+O_2 \rightarrow FMN+RCOOH+H_2O+h\nu$;

where R=alkyl (Baldwin et al. (1975): Bacterial Luciferase. Binding of Oxidized Flavin Mononucleotide. *J. Biol. Chem.*, 250, 2763). The NADH is the primary electron donor in this reaction. The electrons are then, via FMN, transferred to the luciferase, resulting in the emission of light. The NADH which forms during the reaction according to the invention can be detected readily in a range of from 1 to 25 μm. The light yield of luciferase is markedly pH-dependent, a range of between pH 7 and pH 8.5 being particularly suitable.

The activity, or the decrease or increase in activity, can also preferably be determined by means of the conversion of the substrate $NAD^+$ into NADH, where the lower, or inhibited, activity of the polypeptide according to the invention is determined with reference to a less sharp increase in fluorescence emitted by the smaller amounts of NADH formed (see also FIG. 1). NADH fluoresces more than $NAD^+$.

To this end, the polypeptide according to the invention is incubated at a suitable concentration, which is preferably between 0.1 and 20 ng/μl, preferably between 0.13 and 10 ng/μl, of the enzyme, with $NAD^+$ at a concentration of from 5 to 400 μM, preferably 10 to 100 μM, and IMP at a concentration of from 5 to 400 μM, preferably from 50 to 300 μM, at a suitable temperature. The IMP concentration is preferably in each case twice as high as the concentration of the substrate $NAD^+$. It must be borne in mind that substrate inhibition can be observed for both substrates, viz. $NAD^+$ and IMP, and the used concentrations of the two substrates should therefore be checked in this respect. The temperature may be in a range of from 8 to 37° C. The measurement is preferably carried out at from 10 to 30° C., room temperature is also suitable in particular. The reaction is carried out in a usual buffer ("assay buffer") which can contain preferably for example 20 to 200 mM KCl, 1 to 5 mM DTE or DTT, 0.01 to 1% BSA, 0.01 to 0.1% Tween 20 and 2 to 10% glycerol and brought to a pH of 8, for example using 25 to 100 mM Tris buffer (see Example 2). However, other buffer compositions in which the polypeptides according to the invention retain their biological activity and can carry out the reaction which they catalyse are also feasible.

The formation of NADH in the course of the reaction is then monitored with reference to the fluorescence at an excitation wavelength of 360 nm and an emission wavelength of 465 nm. The increase in fluorescence in the presence of a chemical compound can then be compared with the increase in fluorescence in the absence of a chemical compound. The comparison then shows whether the increase in fluorescence in the presence of a chemical compound is less or, if appropriate, more pronounced than in the absence of the chemical compound, i.e. whether said compound has an activatory or inhibitory effect on the polypeptide which is being assayed. The period within which the increase in fluorescence is measured can be varied. A slow increase in fluorescence can be observed over the course of several hours, until, after 5 to 10 hours, a plateau is reached (see also FIG. 3). As a rule, the fluorescence decreases thereafter. However, this slow conversion rate is known from the literature and appears to be characteristic of IMP dehydrogenases. However, it is therefore important to choose the buffer in which the enzyme is stored or the reaction carried out in such a way that stabilization of the polypeptide according to the invention is optimal. Such a buffer should contain for example KCl, BSA, DTT or DTE and glycerol in a suitable concentration. The pH is preferably brought to 8. 10–200 mM KCl, 10–200 mM Tris, 0.02–0.2% BSA and 0.1–5 mM DTE or DTT and 12–25% glycerol are preferably used.

The measurement can also be carried out in formats conventionally used for HTS or UHTS assays, for example in microtitre plates, into which for example a total volume of 5 to 50 μl is introduced per reaction or per well and the individual components are present in one of the above-stated final concentrations. The compound to be assayed and which potentially inhibits or activates the activity of the enzyme (candidate molecule) is introduced for example in a suitable concentration in the above-stated IMP-containing assay buffer. The polypeptide according to the invention is then added in the abovementioned assay buffer containing the second substrate $NAD^+$, thus starting the reaction. The mixture is then incubated for example for up to 2 or 3 hours at a suitable temperature, and the increase in fluorescence is measured at an excitation wavelength of 360 nm and an emission wavelength of 460 nm.

A further measurement is carried out in a corresponding mixture, but without addition of a candidate molecule and without addition of a polypeptide according to the invention (negative control). Another measurement, in turn, is carried out in the absence of a candidate molecule, but in the presence of the polypeptide according to the invention (positive control). The negative and the positive controls thus provide the reference values for the mixtures in the presence of a candidate molecule.

To determine optimal conditions for a method for identifying IMPDH inhibitors or for determining the activity of the polypeptides according to the invention, it may be advantageous to determine the $K_M$ value of the polypeptide according to the invention used. This value provides information on the concentration of the substrate(s) to be used by preference. In the case of the *U. maydis* IMPDH, a $K_M$ of 25 μM was determined (see FIG. 4).

Compounds which inhibit the IMP dehydrogenases according to the invention, in particular the *U. maydis* IMPDH as shown in SEQ ID NO: 2 or SEQ ID NO: 4, were identified with the aid of the method described hereinabove by way of example (see Examples 1 and 3).

Table II shows examples of compounds which were identified as IMPDH inhibitors using the method according to the invention.

The pI50 value shown in this table is the negative decimal logarithm of what is known as the IC50 value which indicates the molar concentration of a substance resulting in 50% inhibition of the enzyme.

A pI50 value of 8, for example, corresponds to half the maximum inhibition of the enzyme at a concentration of 10 nM.

TABLE II

| Example | Compound | pI50 |
|---|---|---|
| 1 | 4-[4-(tetradecyloxy)phenyl]butanoic acid | 4.6 |
| 2 | 3-methoxy-1,2-naphthoquinone | 4.9 |
| 3 | 1,4-dimethyl-1,2,3,4-tetrahydropyrazino[2,3-b]phenazine | 5.0 |
| 4 | 2,3,5,6-tetra(furan-2-yl)furo[3,2-b]furo[3',2':4,5]pyrazine | 6.7 |

It has further been demonstrated within the scope of the present invention that the inhibitors of an IMPDH according to the invention which have been identified with the aid of a method according to the invention are capable of damaging or destroying phytopathogenic fungi.

To this end, a solution of the active compound to be tested was pipetted for example into the wells of microtitre plates. After the solvent had evaporated, medium was added to each well. The medium was previously treated with a suitable concentration of spores or mycelia of the test fungus. The resulting concentrations of the active compound are, for example, 0.1, 1, 10 and 100 ppm.

The plates were subsequently incubated on a shaker at a temperature of 22° C. until sufficient growth was discernible in the untreated control.

The plates were evaluated photometrically at a wavelength of 620 nm. The dose of active compound which leads to a 50% inhibition of the fungal growth over the untreated control ($ED_{50}$) was calculated from the readings of the different concentrations.

The present invention therefore also relates to modulators of the polypeptides according to the invention, in particular compounds or extracts which are suitable for modulating the U. maydis IMPDH as shown in SEQ ID NO: 2 or SEQ ID NO: 4 and which are found with the aid of one of the methods for identifying IMPDH modulators described in the present application.

The present invention furthermore comprises methods of finding chemical compounds which modify the expression of the polypeptides according to the invention. Such "expression modulators", too, may be new fungicidal active compounds. Expression modulators can be small organochemical molecules, peptides or antibodies which bind to the regulatory regions of the nucleic acids encoding the polypeptides according to the invention. Moreover, expression modulators may be small, organochemical molecules, peptides or antibodies which bind to a molecule which, in turn, binds to regulatory regions of the nucleic acids encoding the polypeptides according to the invention, thus influencing their expression. Expression modulators may also be antisense molecules. The present invention likewise relates to the use of modulators of the polypeptides according to the invention or to their expression as fungicides (see Example 3).

The present invention likewise relates to expression modulators of inosine monophosphate dehydrogenases which are found with the aid of the above-described methods of finding expression modulators.

The invention furthermore relates to antibodies which bind specifically to the polypeptides according to the invention or fragments of these. Such antibodies are raised in the customary manner. For example, such antibodies may be produced by injecting a substantially immunocompetent host with an amount of a polypeptide according to the invention or a fragment thereof which is effective for antibody production, and subsequently obtaining this antibody. Furthermore, an immortalized cell line which produces monoclonal antibodies may be obtained in a manner known per se. The antibodies may be labelled with a detection reagent, if appropriate. Preferred examples of such a detection reagent are enzymes, radiolabelled elements, fluorescent chemicals or biotin. Instead of the complete antibody, fragments which have the desired specific binding properties may also be employed.

EXAMPLES

Example 1

Cloning, Expression and Purification of imp1 or Imp1 from *Ustilago maydis*

To clone and express imp1, the ORF from *U. maydis* mRNA was amplified using gene-specific primers as shown in SEQ ID NO: 5 and 6. The corresponding cDNA, an amplicon 1675 bp in length, was inserted into the vector pCRTOP2.1 from Invitrogen (intermediate cloning) and subsequently cloned into the EcoRV- and NotI-cut vector pET32a (Novagen) via the EcoRV and NotI cleavage sites introduced by the primers. The resulting plasmid p830 contains the complete coding sequence of imp1 in N-terminal fusion with the thioredoxin-tag, which is part of the vector. The Imp 1 fusion protein has a calculated mass of 78 kD.

For the heterologous expression, the plasmid p830 was transformed into BL21::DE3 in such a way that the transformation mixture acted directly as preculture in 50 ml of selection medium. These cells were incubated overnight at 37° C. and subsequently diluted 1:100 in selection medium (LB medium supplemented with 100 µg/ml ampicillin). To repress the basal activity of the T7 promoter, 0.2% of glucose was added to the medium. At an $OD_{600\ nm}$ of 0.8–1.0, the temperature of the cells was lowered to 16° C., and the cells were induced after 10 minutes with 1 mM IPTG (final concentration). The cells were harvested after 1.5 h. It was possible to store the cell pellets for several months at −80° C. without suffering a loss of activity. The cells were disrupted by sonifying in lysis buffer (200 mM KCl, 10 mM imidazole, 50 mM Tris-HCl, pH 8, 15% glycerol). Purification was as described in the manufacturer's protocol for Ni-NTA columns (see also FIG. 2). The buffer of the purified protein was exchanged for storage buffer (200 mM KCl, 50 mM Tris-HCl, pH 8, 0.1% BSA, 1 mM DTE, 17% glycerol). In this way, approximately 4 mg of soluble protein were isolated from one litre of culture medium, and this protein was used in methods for identifying IMPDH modulators.

Example 2

(A) Identification of IMP Dehydrogenase Modulators in 384-Well MTP 384-well microtitre plates from Greiner were used for identifying modulators of the *U. maydis* IMPDH (Imp1).

The negative control was pipetted into the first column. The negative control was composed of 5 µl of assay buffer (100 mM KCl, 50 mM Tris/HCl, pH 8, 2 mM DTE, 0.1% BSA, 0.05% Tween 20, 5% glycerol) with 5% DMSO, 20 µl of assay buffer with 200 µM IMP and 25 µl of assay buffer with 100 µM $NAD^+$.

The positive control was pipetted into the second column. The positive control was composed of 5 µl of assay buffer with 5% DMSO, 20 µl of assay buffer with 200 µM IMP and 2 ng/µl IMPDH, and 25 µl of assay buffer with 100 µM $NAD^+$.

A test substance in a concentration of 2 µM in DMSO was introduced into the remaining columns, the assay buffer containing 200 µM IMP being used for diluting the substance to a volume of 5 µl. After addition of 20 µl of assay buffer containing 200 µM IMP and 2 ng/µl IMPDH, 25 µl of assay buffer containing 100 mM $NAD^+$ were added to initiate the reaction. This was followed by incubation at room temperature for 2 hours.

The NADH which was produced during the reaction was measured by determining the absolute fluorescence in a Tecan Ultra fluorescence spectrometer suitable for MTP.

(B) Identification of IMP Dehydrogenase Modulators in 1536-well MTP

The method was carried out as described above, but the total volume of the mixtures was now only 8 µl. The individual components were adapted in a suitable manner.

Example 3

Demonstration of the Fungicidal Effect of the IMPDH Inhibitors Identified

A methanolic solution of the active compound identified with the aid of a method according to the invention, treated with an emulsifier, was pipetted into the wells of microtitre plates. After the solvent had evaporated, 200 µl of potato dextrose medium were added to each well. Suitable concentrations of spores or mycelia of the test fungus (see Table III) were previously added to the medium.

The resulting active compound concentrations were 0.1, 1, 10 and 100 ppm. The resulting emulsifier concentration was 300 ppm.

The plates were subsequently incubated on a shaker at a temperature of 22° C. until sufficient growth was observed in the untreated control. Evaluation was done photometrically at a wavelength of 620 nm. The dose of active compound which leads to a 50% inhibition of the fungal growth over the untreated control ($ED_{50}$) is calculated from the readings of the different concentrations. Compound 3 of Table II showed a suitable effect even at the application rates shown in Table III.

TABLE III

| Organism | $ED_{50}$ [ppm] |
| --- | --- |
| Brotytis cinerea | 27.7 |
| Giberella zeae | 60.3 |
| Phytophthora cryptogea | 55.1 |
| Septoria tritici | 43.4 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

The invention claimed is:

1. A method of identifying one or more fungicides which are capable of controlling phytopathogenic fungi which attack and damage plants, plant parts or plant products or reduce their yield or value comprising (a) contacting an inosine 5'-monophosphate dehydrogenase having the amino acid sequence of SEQ ID NO: 2 or 4 with a chemical compound or a mixture of chemical compounds, (b) comparing the ability of the inosine 5'-monophosphate dehydrogenase to catalyse the conversion of inosine 5'-monophosphate into xanthosine 5'-monophosphate in the presence of the chemical compound or the mixture of chemical compounds with the ability of an inosine 5'-monophosphate dehydrogenase to catalyse the conversion of inosine 5'-monophosphate into xanthosine 5'-monophosphate in the absence of the chemical compound or the mixture of chemical compounds, wherein the ability of the inosine 5'-monophosphate dehydrogenase to catalyze the conversion of inosine 5' monophosphate into xanthosine 5'-monophosphate is determined by photospectrometrically monitoring the conversion of the substrate NAD+ into NADH, (c) determining if said chemical compound or said mixture of chemical compounds inhibits the ability of the inosine 5'-monophosphate dehydrogenase to catalyse the conversion of inosine 5'-monophosphate into xanthosine 5'-monophosphate, wherein said ability to inhibit the conversion of the inosine 5'-monophosphate into xanthosine 5"-monophosphate indicates that the chemical compound or the mixture of chemical compounds is a fungicide, and (d) verifying the fungicidal action of the compound or the mixture of chemical compounds by bringing it into contact with one or more phytopathogenic fungi.

2. A method according to claim 1, wherein the conversion of the substrate $NAD^+$ into NADH is monitored by coupling the reaction catalysed by the inosine 5'-monophosphate dehydrogenase with the reaction catalysed by a NADH-FMN oxidoreductase.

3. A method according to claim 1, wherein a host cell containing and expressing a nucleic acid which encodes an inosine 5'-monophosphate dehydrogenase having the amino acid sequence of SEQ ID NO: 2 or 4 is contacted with said chemical compound or said mixture of chemical compounds.

4. A method of identifying one or more fungicides which are capable of controlling *Ustilago maydis* comprising (a) contacting an inosine 5-monophosphate dehydrogenase from *Ustilago maydis* having the amino acid sequence of SEQ ID NO: 2 or 4 with a chemical compound or a mixture of chemical compounds, (b) comparing the ability of the inosine 5'-monophosphate dehydrogenase to catalyse the conversion of inosine 5-monophosphate into xanthosine 5'-monophosphate in the presence of the chemical compound or the mixture of chemical compounds with the ability of an inosine 5-monophosphate dehydrogenase to catalyse the conversion of inosine 5-monophosphate into xanthosine 5'-monophosphate in the absence of the chemical compound or the mixture of chemical compounds, wherein the ability of the inosine 5'-monophosphate dehydrogenase to catalyze the conversion of inosine 5' monophosphate into xanthosine 5'-monophosphate is determined by photospectrometrically monitoring the conversion of the substrate NAD+ into NADH, (c) determining if said chemical compound or said mixture of chemical compounds inhibits the ability of the inosine 5'-monophosphate dehydrogenase to catalyse the conversion of inosine 5'-monophosphate into xanthosine 5'-monophosphate, wherein said ability to inhibit the conversion of the inosine 5'-monophosphate into xanthosine 5"-monophosphate indicates that the chemical compound or the mixture of chemical compounds is a fungicide, and (d) verifying the fungicidal action of the compound or the mixture of chemical compounds by bringing it into contact with one or more phytopathogenic fungi.

* * * * *